United States Patent
Tonna et al.

(10) Patent No.: US 10,262,110 B2
(45) Date of Patent: Apr. 16, 2019

(54) SYSTEMS AND METHODS FOR MANAGING PATIENT DEVICES

(71) Applicant: University of Utah Research Foundation, Salt Lake City, UT (US)

(72) Inventors: Joseph Tonna, Salt Lake City, UT (US); Benjamin Brooke, Salt Lake City, UT (US); Julia Beynon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/354,724

(22) Filed: Nov. 17, 2016

(65) Prior Publication Data

US 2017/0229006 A1 Aug. 10, 2017

Related U.S. Application Data

(60) Provisional application No. 62/256,449, filed on Nov. 17, 2015.

(51) Int. Cl.
*G06F 19/00* (2018.01)
*G16H 40/20* (2018.01)
*G08B 25/00* (2006.01)

(52) U.S. Cl.
CPC ......... *G06F 19/3418* (2013.01); *G16H 40/20* (2018.01); *G08B 25/005* (2013.01); *G08B 25/006* (2013.01)

(58) Field of Classification Search
CPC .... G06F 19/3418; A61B 5/0002; G08B 25/00
USPC ..... 340/506, 527, 539.1, 573.1, 572.1–572.9
See application file for complete search history.

(56) References Cited

U.S. PATENT DOCUMENTS

| | | | |
|---|---|---|---|
| 8,837,683 | B2 | 9/2014 | Conroy |
| 8,842,001 | B2 | 9/2014 | Gilham et al. |
| 2006/0089539 | A1 | 4/2006 | Miodownik et al. |
| 2008/0021731 | A1* | 1/2008 | Rodgers ............... A61B 5/1113 705/2 |
| 2011/0117878 | A1* | 5/2011 | Barash ................... H04W 4/90 455/404.2 |
| 2011/0230161 | A1 | 9/2011 | Newman |
| 2012/0000464 | A1 | 1/2012 | Gajic et al. |

(Continued)

OTHER PUBLICATIONS

Critical Response Systems, Inc.; "Alarm Notification—HealthcareWp"; Critical Response Systems; (2014); 13 pages; Document 11-094, Version 1.15.

(Continued)

*Primary Examiner* — Phung Nguyen
(74) *Attorney, Agent, or Firm* — Thorpe North & Western, L.L.P

(57) ABSTRACT

An alarm manager identifies responders that are confirmed to be available to receive an alarm notification pertaining to a patient device through one or more computing devices. An alarm of the patient device may be suppressed in response to verifying that responders are available to receive the alarm notification. The alarm notification may be transmitted to the identified responders, and verification of receipt, acceptance, and/or completion of the alarm notification is received. An alarm notification may be retransmitted in response to a failure to verify receipt, acceptance, and/or completion within a time threshold.

20 Claims, 7 Drawing Sheets

(56) References Cited

U.S. PATENT DOCUMENTS

| | | | | |
|---|---|---|---|---|
| 2015/0035679 A1* | 2/2015 | Gilham | .................. | A61B 5/746 340/573.1 |
| 2015/0187202 A1* | 7/2015 | Janssen | .................. | G16H 40/63 340/573.1 |

OTHER PUBLICATIONS

Critical Response Systems, Inc.; "Response Paging for Hospitals—HealthcareOverview"; Critical Response Systems; (2014); 2 pages.

Extension Healthcare; "Extension Engage™ | Extension Healthcare"; Healthcare IT Marketplace; (Upon knowledge and belief prior to Jul. 15, 2015); 1 page; [retrieved on Oct. 29, 2018]; Retrieved from <URL: https://www.health-care-it.com/company/622638/products/215546/extension-engage >.

Extension Healthcare; "Extension Engage™ Mobile | Extension Healthcare"; Healthcare IT Marketplace; (Upon knowledge and belief prior to Jul. 15, 2015); 1 page; [retrieved on Oct. 29, 2018]; Retrieved from <URL: https://www.health-care-it.com/company/622638/products/215547/extension-engage-mobile >.

Mobile Heartbeat™; "Mobile Heartbeat Overview"; Mobile Heartbeat™ Clinical Communications; (Apr. 8, 2015); 2 pages; <URL: http://mobileheartbeat.com/wordpress/products/mobile-heartbeat-overview/>.

Voalte; "Voalte Products—Voalte"; (Mar. 3, 2015); 4 pages; <URL: http://www.voalte.com/products >.

Vocera; "Vocera Alarm Management & Analytics | Vocera"; Vocera Communications, Inc.; (Apr. 1, 2015); 3 pages; <URL: http:www.vocera.com/resource/vocera-alarm-management-analytics >.

Vocera; "Vocera Unveils Alarm Management and Analytics Solutions to Reduce Alarm Fatigue | Vocera"; Vocera Communications, Inc.; (Jul. 22, 2014); 3 pages; [retrieved on Oct. 29, 2018]; Retrieved from <URL: https://www.vocera.com/press-release/vocera-unveils-alarm-management-and-analytics-solutions-reduce-alarm-fatigue >.

\* cited by examiner

SYSTEMS AND METHODS FOR MANAGING PATIENT DEVICES

CROSS-REFERENCE TO RELATED APPLICATIONS

This application claims priority to U.S. Provisional Application No. 62/256,449, which was filed on Nov. 17, 2015, and which is hereby incorporated by reference.

TECHNICAL FIELD

This disclosure relates to systems and methods for managing alarm notifications and, in particular, to managing alarm notifications pertaining to devices being used to provide healthcare services to a patient.

BACKGROUND

Healthcare services typically involve provisioning care to patients using one or more patient devices. As used herein, a "patient device" refers to any device, machine, and/or computing system for providing healthcare-related services, such as patient monitoring, patient care, and/or the like. A patient device may include any device used to perform a monitoring function pertaining to a patient, including, but not limited to: a device configured to monitor physiological characteristics of a patient (e.g., vital signs), a pulse oximetry ($SpO_2$) device, a heart monitoring device (e.g., heart rate monitor), an electrocardiograph (ECG) device, an electroencephalograph (EEG) device, a blood pressure monitoring device (e.g., an invasive or non-invasive blood pressure monitoring device), a body temperature monitoring device, a cardiac output monitoring device, a capnography ($CO_2$) monitoring device, a respiration monitoring device, and/or the like. Alternatively, or in addition, as used herein, a patient device may refer to a device configured to perform a healthcare-related function for a patient, including, but not limited to: a therapy device, a drug delivery device, an intravenous therapy device, a respiration device (e.g., an oxygen delivery device, a sleep-apnea device, and/or the like), a heart assistance device (e.g., a pacemaker), a renal assist device (e.g., a dialysis machine), a liver support device, and/or the like.

Patient devices may generate outputs including, but not limited to: audio outputs, visual outputs, and/or the like. A patient device may be configured to generate status outputs. As used herein, a "status output" refers to an output pertaining to the nominal operation of a patient device. A status output may refer to a so-called "heartbeat" output indicating that the patient device is functioning within particular bounds (e.g., is turned on and/or is operating nominally). A patient device may be further configured to generate alarm outputs. As used herein, an "alarm output" refers to an output triggered by an alarm condition. An alarm condition refers to a condition and or event pertaining to the patient device including, but not limited to: a condition pertaining to a monitoring function of the patient device (e.g., monitoring a heart rate value that falls below a threshold), a condition pertaining to a healthcare function of the patient device (e.g., an amount of medication available to be dispensed from a drug dispensing device falling below a threshold), a condition pertaining to the patient device itself (e.g., power loss, power noise, network connectivity loss, wear level), and/or the like.

Patient devices may be placed in close proximity to a patient. The outputs generated by the patient devices may disturb the patient. For example, outputs of patient devices in a hospital room may prevent patients from sleeping properly, which may adversely impact the health of the patients. Some outputs generated by patient devices may not be important to the care of the patient. Moreover, alarm outputs generated by the patient devices themselves (e.g., in a particular patient's room) may not be readily detected by health care providers, and there may be no way of ensuring that the conditions which raised the alarm are resolved within an acceptable time frame. Therefore, what are needed are systems and methods for managing outputs of patient devices that reduce disturbances to the patient. In addition, systems and methods for routing alarms to appropriate personnel, ensuring that the alarms are received, and/or verifying that conditions giving rise to the alarms are resolved are also needed.

SUMMARY

Disclosed herein are embodiments of systems and methods for managing patient devices. In one embodiment, a patient device management system comprises an integration module configured to monitor a patient device for detection of an alarm condition at the patient device, an alarm manager configured to select a computing device to receive an alarm notification pertaining to the detected alarm condition from a plurality of computing devices, each computing device being registered to a responder assigned to receive alarms of specified patient devices, wherein selecting the computing device comprises identifying a registered computing device that is registered to a responder assigned to receive alarms of the patient device, and a communication layer configured to verify receipt of the alarm notification by the responder at the selected computing device.

The alarm manager may be configured to maintain alarm routing data on a non-transitory storage medium, the alarm routing data comprising network address data of the registered computing devices, wherein the alarm routing data comprises availability data that distinguishes registered computing devices that are available to receive alarm notifications via an electronic communication network from registered computing devices that are unavailable to receive alarm notifications via the electronic communication network. The communication layer may be configured to transmit availability requests to network addresses of the registered computing devices, and the alarm manager may be configured to update the alarm routing data in response to the transmitted availability requests. Updating the alarm routing data may comprise recording that the registered computing device is unavailable to receive alarm notifications in response to failing to receive a response within a response time threshold, recording that the registered computing device is available to receive alarm notifications in response to receiving a response within the response time threshold, recording that the registered computing device is available to receive alarm notifications for a particular responder in response to validating an authentication credential of the particular responder within the response time threshold. The alarm manager may be configured to select the computing device by identifying, in the alarm routing data, a registered computing device that is available to receive alarm notifications via the electronic communication network and is registered to a responder assigned to receive alarms of the patient device. The alarm manager may be configured to register a particular computing device to a responder in the alarm routing data in response to verifying an authentication credential of the responder received from the particular computing device through the electronic communication network.

Embodiments of the system disclosed herein may further comprise an alarm notification application configured for operation on the selected computing device. The alarm notification application may be configured to transmit an acknowledgement message to the communication layer via an electronic communication network in response to receiving the alarm notification. The alarm notification application may be embodied as machine-readable instructions stored on a non-transitory storage medium. The alarm notification application may be configured to receive alarm notifications transmitted thereto through the electronic communication network, display received alarm notifications on a display interface of the computing device, authenticate alarm notifications received via the electronic communication network, verify receipt of alarm notifications. The alarm notification application may further comprise user interface elements to enable a responder to acknowledge receipt of alarm notifications, accept responsibility for alarm notifications, provide an estimated time of arrival for responding to alarm notifications, confirm completion of an alarm notifications, and so on. The alarm notification application may be configured to authenticate responders to the patient management system (e.g., request and/or transmit authentication credentials of the responder and/or computing device to the patient management system). The alarm notification application may be further configured to transmit responder messages to the patient device management system to, inter alia, acknowledge receipt of alarm notifications, verify that alarm notifications have been viewed by a responder, provide an estimated response time to an alarm notification, verify acceptance of responsibility of an alarm notification, confirm completion of an alarm notification, and/or the like. The alarm notification application may be configured for operation on any suitable computing device including, but not limited to: a personal computing device, a mobile computing device, a smart phone, a personal digital assistant, a general-purpose computing device, a special purpose computing device (e.g., a dedicated monitoring terminal), and/or the like.

The communication layer may be configured to verify receipt of the alarm notification by the responder at the selected computing device in response to receiving a message from the selected computing device through the electronic communication network. The communication layer may be configured to verify receipt of the alarm notification by the responder at the selected computing device in response to authenticating the responder at the selected computing device. The alarm manager may be configured to select a different one of the registered computing devices to receive the alarm notification in response to determining that the communication module has failed to verify receipt of the alarm notification by the responder at the selected computing device. In some embodiments, the alarm manager is configured to determine that a time elapsed since detection of the alarm condition at the patient device exceeds a time threshold, and wherein, in response, the alarm manager is configured to transmit a new, different alarm notification to one or more of the registered computing devices other than the selected computing device.

Embodiments of the system disclosed herein may comprise an alarm assignment module configured to record data on a non-transitory storage medium identifying the responder assigned to the alarm notification in response to authenticating an alarm acceptance message from the responder. In some embodiments, the alarm manager is configured to determine that a time elapsed since detection of the alarm condition at the patient device exceeds a time threshold, and wherein, in response, the alarm manager is configured to transmit a new, different alarm notification to one or more of the registered computing devices other than the selected computing device.

The alarm manager may be configured to identify a set of one or more responders designated to respond to alarms of the patient device, and to generate an alarm notification to transmit to the one or more responders using the communication layer, wherein the alarm notification comprises a request for one or more of: verification of receipt of the alarm notification, acceptance of responsibility for the alarm notification, and confirmation that the alarm condition of the alarm notification has been resolved.

Embodiments of the system disclosed herein may further comprise an alarm device that is separate from the patient device. The alarm manager may be configured to activate the alarm device in response to determining that requested verification of receipt of the alarm notification has not been received by the communication layer within a receipt verification threshold, determining that requested acceptance of responsibility for the alarm notification has not been received by the communication layer within an acceptance threshold, determining that requested confirmation of resolution of the alarm notification has not been received within a resolution threshold, and/or determining that a time elapsed since detection of the alarm condition at the patient device exceeds an alarm duration threshold. The alarm device may comprise one or more of an audio output device and a display device, and may be placed on an exterior of a room housing the patient device. The alarm device may comprise a graphical user interface on a computing device display, wherein activating the alarm device comprises displaying the alarm notification on the graphical user interface.

Embodiments of the system disclosed herein further comprises an alarm processing module configured to identify a patient corresponding to the alarm notification, and an alarm routing module configured to determine one or more responders assigned to receive alarms pertaining to the identified patient. Selecting the computing device to receive the alarm notification may comprise selecting a registered computing device associated with one of the determined responders. The alarm processing module may be configured to identify a patient area corresponding to the alarm notification. Selecting the computing device to receive the alarm notification may comprise selecting a registered computing device associated with one of the determined responders.

In some embodiments, the communication layer is configured to verify receipt of the alarm notification by the responder at the selected computing device by transmitting the alarm notification to the selected computing device via an electronic communication network and receiving an acknowledgement through the electronic communication network that the alarm notification was displayed on a display device of the selected computing device. The communication layer may be further configured to verify receipt of the alarm notification in response to authenticating a message from the selected computing device indicating that the alarm notification was viewed by the designated responder on the display device of the selected computing device.

The alarm manager may be configured to assign criticality levels to alarm notifications based on one or more of:

characteristics of patients corresponding to the alarm notifications, characteristics of patient devices corresponding to the alarm notifications, and alarm conditions corresponding to the alarm notifications. The alarm notification may indicate the assigned criticality level. The alarm manager may be configured to select a plurality of registered computing devices to receive the alarm notification in response to assigning a high criticality level to the alarm notification. The alarm manager may be configured to transmit the alarm notification to one or more additional registered computing devices, other than the selected computing device, in response to determining that the communication layer has failed to verify receipt of the alarm notification at the selected computing device within a time threshold, and wherein the time threshold corresponds to the criticality level assigned to the alarm notification. The alarm manager may be configured to activate an alarm system of the patient device in response to determining that the communication layer has failed to verify receipt of the alarm notification at the selected computing device within a time threshold, wherein the time threshold is set in accordance with the criticality level assigned to the alarm notification. In some embodiments, the alarm manager is configured to assign an action type to the alarm notification, the assigned action type indicating an action required to resolve the alarm condition, wherein the responders are certified to perform specified action types, and wherein selecting the computing device to receive the alarm notification further comprises selecting a registered computing device associated with a responder that is certified to perform the action type assigned to the alarm notification. The patient device configuration manager may configure the patient device to silence an audio output of the patient device in response to verifying access to operating state data of the patient device.

The system may further comprise a patient device configuration manager that configures the patient device to silence an alarm output of the patient device in response to the alarm manager identifying one or more computing devices that are available to receive alarm notifications pertaining to the patient device. Embodiments of the system disclosed herein may further comprise an alarm device comprising an alarm output, wherein the alarm manager is configured to selectively activate the alarm output in response to detection of alarm conditions at the patient device, and a patient device configuration manager that configures the patient device to silence an alarm output of the patient device in response to determining that the alarm manager is configured to selectively activate the alarm output of the alarm device in response to detection of alarm conditions at the patient device.

The patient device integration module may be configured to capture operating state data from a plurality of patient devices. The system may include a display module configured to generate an interface combining portions of the operating state data captured from the plurality of patient devices and to present the generated interface on a computing device display.

Disclosed herein are embodiments of a method for managing patient devices. Portions of the steps and/or operations of the method disclosed herein may be implemented by use of hardware components, such as a processor, memory, non-transitory storage, a network link, a network interface, input/output devices, and/or the like. Alternatively, or in addition, portions of the steps and/or operations of the method disclosed herein may be embodied as instructions stored on a non-transitory storage medium. The instructions may be configured to execution by a computing device and may configured the computing device to perform certain steps and/or operations disclosed herein.

Embodiments of the disclosed method may comprise monitoring a patient device to detect an alarm condition at the patient device, selecting a computing device to receive an alarm notification pertaining to the detected alarm condition from a plurality of computing devices, each computing device being registered to a responder assigned to receive alarms of specified patient devices, wherein selecting the computing device comprises identifying a registered computing device that is registered to a responder assigned to receive alarms of the patient device, and verifying receipt of the alarm notification by the responder at the selected computing device.

The method may further comprise maintaining alarm routing data on a non-transitory storage medium, the alarm routing data comprising network address data of the registered computing devices, wherein the alarm routing data comprises availability data that distinguishes registered computing devices that are available to receive alarm notifications via an electronic communication network from registered computing devices that are unavailable to receive alarm notifications via the electronic communication network. Updating the alarm routing data in response to transmitting an availability request to a network address of a registered computing device via the electronic communication network may comprise one or more of: recording that the registered computing device is unavailable to receive alarm notifications in response to failing to receive a response within a response time threshold, recording that the registered computing device is available to receive alarm notifications in response to receiving a response within the response time threshold, and/or recording that the registered computing device is available to receive alarm notifications for a particular responder in response to validating an authentication credential of the particular responder within the response time threshold. Selecting the computing device may comprise identifying, in the alarm routing data, a computing device that is available to receive alarm notifications via the electronic communication network and is registered to a responder that is assigned to receive alarms of the patient device. The method may further comprise recording data on a non-transitory storage medium identifying the responder assigned to the alarm notification in response to authenticating an alarm acceptance message from the responder.

Embodiments of the method disclosed herein may further comprise registering a particular computing device to a responder in the alarm routing data in response to verifying an authentication credential of the responder received from the particular computing device through the electronic communication network. Verifying receipt of the alarm notification by the responder at the selected computing device comprises receiving a message from the selected computing device through an electronic communication network. Alternatively, or in addition, verifying receipt of the alarm notification by the responder at the selected computing device comprises authenticating the responder at the selected computing device. In some embodiments, the method comprises selecting a different one of the registered computing devices to receive the alarm notification in response a failure to verify receipt of the alarm notification by the responder at the selected computing device within a time threshold. The method may further include transmitting a new, different alarm notification to one or more of the registered computing devices other than the selected computing device in response to determining that a time elapsed since detection of the alarm condition at the patient device exceeds a time threshold.

In some embodiments, the method further comprises activating an alarm device that is separate from the patient device in response to one or more of determining that requested verification of receipt of the alarm notification has not been received by the communication layer within a receipt verification threshold, determining that requested acceptance of responsibility for the alarm notification has not been received by the communication layer within an acceptance threshold, determining that requested confirmation of resolution of the alarm notification has not been received within a resolution threshold, and/or determining that a time elapsed since detection of the alarm condition at the patient device exceeds an alarm duration threshold. The alarm device may comprise one or more of an audio output device and a visual output, and wherein the alarm device is placed on an exterior of a room housing the patient device. The alarm device may comprise a graphical user interface presented on a computing device display, and wherein activating the alarm device comprises displaying the alarm notification on the graphical user interface.

Embodiments of the disclosed method may further comprise assigning a criticality level to the alarm notification, and selecting one or more responders assigned to receive alarms pertaining to the patient based on the assigned criticality level. Assigning the criticality level may comprise evaluating state data of the patient device pertaining to the detected alarm condition. Alternatively, or in addition, assigning the criticality level may comprise identifying one or more other alarm conditions pertaining to a patient corresponding to the alarm condition. In one embodiment, assigning the criticality level comprises matching a condition of a patient corresponding to the alarm condition to the detected alarm condition. Assigning the criticality level may comprise applying one or more alarm evaluation rules encoded on a machine-readable storage medium, wherein the alarm evaluation rules comprise analyzing one or more of state data of the patient device, patient data of a patient associated with the detected alarm condition, and one or more other detected alarm conditions associated with the patient.

The method disclosed herein may further comprise assigning a response type to the alarm notification, and selecting one or more responders assigned to receive alarms pertaining to the patient based on the assigned response type. Assigning the response type may comprise matching an identifier of patient device to one of a plurality of pre-defined response types recorded on a non-transitory storage medium. Alternatively, or in addition, assigning the response type may comprise evaluating one or more alarm evaluation rules encoded on a machine-readable storage medium, wherein the alarm evaluation rules comprise analyzing one or more of state data of the patient device, patient data of a patient associated with the detected alarm condition, and one or more other detected alarm conditions associated with the patient.

Embodiments of the method disclosed herein may comprise assigning a criticality level and response type to the alarm notification. Selecting the computing device to receive the alarm notification may comprise identifying responder records having responder data matching the assigned criticality level and the assigned response type, and selecting a computing device registered to one or more of the identified responder records that is available to receive alarm notifications via an electronic communication network.

The method may further include transmitting availability requests to network addresses of the registered computing devices, and updating the alarm routing data in response to the transmitted availability requests. The method may further comprise suppressing an alarm output of the patient device in response to identifying a computing device available to receive alarm notifications pertaining to the patient device and/or suppressing a status output of the patient device in response to accessing state data of the patient device.

In some embodiments, the method further comprises transmitting the alarm notification to the selected computing device through an electronic communication network. Transmitting the alarm notification may comprise one or more of establishing a network connection to the selected computing device through the electronic communication network, transmitting the alarm notification to the selected computing device in response to a request from the selected computing device received through the electronic communication network, and sending the alarm notification to the selected computing device through a messaging network.

Some embodiments of the method disclosed herein may comprise generating an alarm notification record to represent an alarm condition detected at a patient device, selecting a responder to receive the generated alarm notification, wherein selecting the responder comprises, evaluating assignment data of responder records stored in a non-transitory data store to identify a set of one or more responder records that are assigned to receive the alarm notification, and selecting a responder record from the identified set based on availability data of contact records registered to the responder records, the availability data identifying computing devices available to receive alarm notifications for the responder through an electronic communication network. The method may further include transmitting electronic data of the alarm notification record to one or more computing devices registered to the selected responder through the electronic communication network, and verifying receipt of the electronic data of the alarm notification record at one or more of the computing devices registered to the selected responder. The method may further comprise verifying availability of contact records registered to the responder records by one or more of receiving data from the computing device through the electronic communication network, and authenticating a credential transmitted from the computing device through the electronic communication network.

Embodiments of the method disclosed herein may comprise configuring the patient device to silence an alarm output of the patient device in response to verifying availability of a contact record of a responder record having alarm assignment data corresponding to the patient device. The method may further comprise monitoring the patient device to detect the alarm condition at the patient device through one or more of a standard interface of the patient device, a proprietary interface of the patient device, and a third-party interface of the patient device. Monitoring the patient device may further comprise acquiring state data from the patient device. The alarm condition may be detected in response to acquiring the state data from the patient device. A status output of the patient device may be suppressed in response to acquiring the state data from the patient device.

Additional aspects and advantages will be apparent from the following detailed description of preferred embodiments, which proceeds with reference to the accompanying drawings.

DETAILED DESCRIPTION

Figure 1:
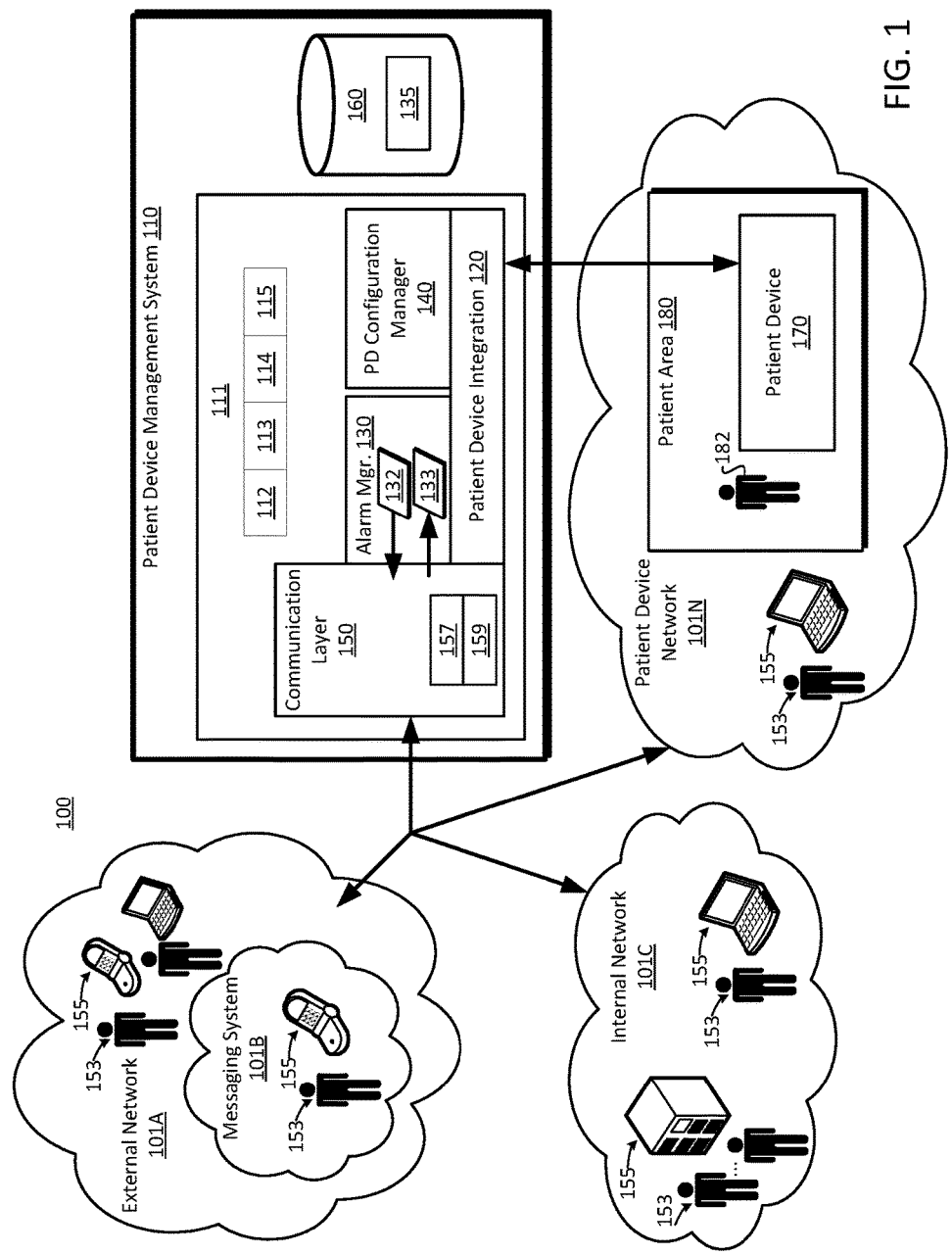
FIG. 1 is a schematic diagram of one embodiment of a system comprising a patient device management system.

FIG. 1 is a schematic block diagram of one embodiment of a system 100 comprising a patient device (PD) management system 110. The PD management system 110 may comprise a computing device 111, which may include, inter alia, processing resources 112, memory resources 113, communication resources 114, storage resources 115, and so on. The processing resources 112 may comprise a central processing unit (CPU), a general purpose processor, a special purpose processor, an application-specific integrated circuit (ASIC), configurable logic, and/or the like. The memory resources 113 may comprise random access memory (RAM), volatile RAM, dynamic RAM, persistent RAM, and/or the like. The communication resources 114 may comprise one or more network links and/or interfaces to communicatively couple the PD management system 110 to one or more electronic communication networks 101A-N. As used herein, an "electronic communication network" or "network" refers to any communication network for the exchange of electronic data. An electronic communication network may include, but is not limited to: a public switched telephone network (PSTN), a cellular data network, a Transmission Control Protocol/Internet Protocol (TCP/IP) network (e.g., the Internet), a Local Area Network (LAN), a Wide Area Network (WAN), a Virtual Private Network (VPN), a Storage Area Network (SAN), a wireless network (e.g., radio, IEEE 802.11), a combination of networks, and/or the like. The PD management system 110 may be communicatively coupled to any number and/or type of electronic communication networks 101A-N, including, but not limited to: an external network 101A, a messaging system 101B, an internal network 101C, a patient device network 101N, and so on.

The PD management system 110 may comprise, inter alia, a PD integration module 120, an alarm manager 130, a PD configuration manager 140, and a communication layer 150. The PD integration module 120 may be configured to communicatively couple the PD management system 110 to patient device(s) 170. The PD integration module 120 may be further configured to monitor for detection of alarm conditions at the patient device(s) 170. The patient device 170 may be located within a particular patient area 180 (e.g., a room, an intensive care unit (ICU), a recovery room, and/or the like), and may be used to provide healthcare-related services to a patient 182. As disclosed in further detail herein, the alarm manager 130 may be configured to handle alarm conditions detected at the patient device 170 by notifying appropriate personnel of the alarm conditions. The alarm manager 130 may be further configured to verify that information about the alarm conditions is being received and/or acknowledged by the appropriate personnel, and that actions to resolve the alarm conditions are being taken. In response, the PD configuration manager 140 may configure the patient device 170 to reduce and/or suppress outputs generated by the patient device 170, such as alarm outputs, status outputs, and so on, which may reduce disturbances to the patient 182.

In response to detection of an alarm condition by the PD integration module 120, the alarm manager 130 may be configured to route a corresponding alarm notification 132 to one or more responders 153. As used herein, an "alarm notification" refers to electronic data comprising information pertaining to an alarm condition detected at a patient device 170. An alarm notification 132 may comprise electronic data embodied on a machine-readable memory, communication network, and/or non-transitory storage system, such as the storage resources 115 of the computing device 111 and/or a storage system 160. As disclosed in further detail herein, an alarm notification 132 may comprise any suitable information pertaining to an alarm condition of a patient device 170. As used herein, a "responder" 153 refers to any entity designated to receive alarm notifications 132. A responder 153 may include, but is not limited to: healthcare personnel providing healthcare services to the patient 182, such as a specialist physician, a primary care physician, a physician's assistant, a nurse, a nurse's aide, a therapist, a counselor, a pharmacist, and/or the like. A responder 153 may further include personnel responsible for the maintenance of patient devices 170, such as maintenance personnel, a technician, and/or the like.

The alarm manager 130 may be configured to route alarm notifications 132 to responders 153 by use of a communication layer 150. The communication layer 150 may be communicatively coupled to one or more electronic communication networks 101A-N. The communication layer 150 may be configured to send alarm notifications 132 to responder(s) 153 by, inter alia, transmitting alarm notifications 132 to computing device(s) 155 registered to the responder(s) 153 via one or more of the electronic communication networks 101A-N. The communication layer 150 may be further configured to request and/or receive responder messages 133 through the electronic communication network(s) 101A-N. The communication layer 150 may use the responder messages 133 to verify receipt of alarm notifications 132, verify that an alarm notification 132 was viewed by a particular responder 153, verify that a responder 153 has accepted an alarm notification 132 (e.g., accepted responsibility for a particular alarm notification 132), confirm that an alarm notification 132 has been completed, and so on. In some embodiments, portions of the communication layer 150 are embodied as machine-executable instructions stored on non-transitory storage resources 115 of the computing device 111. In some embodiments, the communication layer 150 comprises network hardware to communicatively couple to one or more of the electronic communication networks 101A-N, which hardware may include, but is not limited to: a network link, a network interface, a hub, a router, a switch, a modem, a wireless transceiver, an antenna, a tuner, and/or the like. The communication layer 150 may further comprise software components embodied on a non-transitory machine-readable storage medium, which components may include, but are not limited to: a network driver, a network protocol, a network stack, a communication framework, and/or the like. Alternatively, or in addition, the communication layer 150 may be communicatively coupled to one or more of the electronic communication networks 101A-N by use of the communication resources 114 of the computing device 111.

The communication layer 150 may be configured to route alarm notifications 132 to responders 153 by, inter alia, transmitting alarm notifications 132 directly to computing devices 155 of the responders 153 (e.g., pushing alarm notifications 132 to designated computing devices 155), transmitting alarm notifications 132 through one or more messaging systems 101B, responding to requests from the computing device(s) 155 (e.g., enabling computing devices 155 to "pull" alarm notifications 132 and/or other information from the PD management system 110), and/or the like. In some embodiments, the PD management system 110 comprises and/or hosts an alarm application 157. The alarm application 157 may comprise machine-executable instructions configured for operation on one or more of the computing devices 155. The alarm application 157 may be configured to receive alarm notifications 132, render and/or display alarm notifications 132 to responders 153 at the computing devices 155, provide inputs for responding to alarm notifications 132, transmit responder messages 133 to the communication layer 150 (e.g., acknowledge receipt, verify display, accept responsibility, and/or confirm completion of alarm notifications 132), and so on. Alternatively, or in addition, the communication layer 150 may comprise a content server 159 configured to serve electronic markup data to computing device(s) 155. The electronic markup data may comprise data to be rendered and/or displayed on the computing devices 155 (e.g., in a browser application operating on a computing device 155). The content server 159 may be configured to transmit electronic markup data of alarm notifications 132 to selected computing devices 155, receive responder messages 133, and so on.

Figure 2:
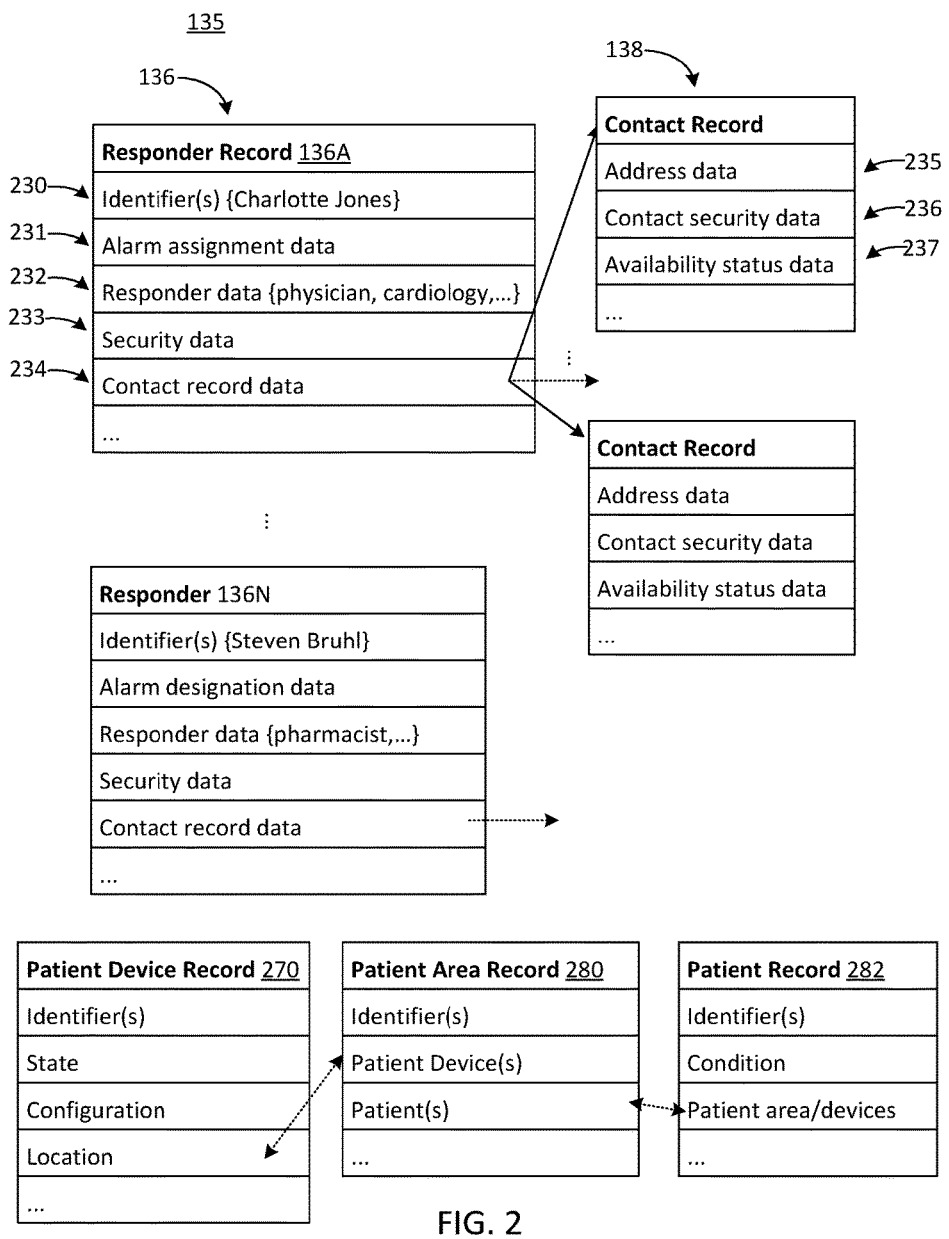
FIG. 2 is a block diagram of embodiments of alarm routing data.

In some embodiments, the alarm manager 130 selects a computing device 155 for an alarm notification 132 by use of alarm routing data 135. FIG. 2 depicts embodiments of alarm routing data 135. The alarm routing data 135 may be embodied as machine-readable data stored on a non-transitory storage medium, such as the storage resources 115 of the computing device 111 and/or the storages system 160. The alarm routing data 135 may be embodied as one or more data structures of a data management system, such as a database storage system, a directory, a file system, and/or the like.

The alarm routing data 135 may comprise responder records 136 comprising information pertaining to responders 153 designated to receive alarm notifications 132 from the PD management system 110. A responder record 136 may correspond to a particular individual (e.g., a particular physician). Alternatively, or in addition, a responder record 136 may represent a group (e.g., janitorial staff, nurses assigned to a particular area, and/or the like). A responder record 136 may include, but is not limited to: identifier(s) 230 of the responder 153 (e.g., name, employee number, description, and/or other identifying information), alarm assignment data 231, responder data 232, security data 233, contact record data 234, and so on. The alarm assignment data 231 may be used to identify alarm notifications 132 to send to the responder 153, such as alarm notifications 132 corresponding to particular patient devices (e.g., patient device 170), alarm notifications 132 corresponding to particular patient area(s) 180 (e.g., a particular room or recovery area), alarm notifications 132 corresponding to particular patient(s) 182, and so on. The alarm assignment data 231 may further indicate times during which the responder 153 is on call to receive alarm notifications 132 and/or times during which the responder 153 is not available to receive such alarms. In some embodiments, the alarm assignment data 231 comprises a set of identifier(s) corresponding to particular patient device(s) 170, particular patient area(s) 180, and/or particular patient(s) 182. The alarm assignment data 231 may reference identifiers and/or data pertaining to the patient device 170, patient area 180, and/or patient 182.

In some embodiments, the alarm assignment data 231 references records pertaining to patient device(s) 170, patient area(s) 180, and/or patient(s) 182. FIG. 2 further illustrates embodiments of a patient device record 270, a patient area record 280, and a patient record 282. A patient device record 270 may comprise information pertaining to a particular patient device (e.g., patient device 170), including, but not limited to: identifier(s) of the patient device, an operating state of the patient device, configuration data, a location of the patient device, and so on. As described in further detail herein, the state of a patient device 170 may indicate the current operating state thereof, including alarm conditions (if any) detected by the patient device 170. The configuration of the patient device record 270 may comprise current configuration data of the patient device 170, including, inter alia, whether alarms of the patient device 170 are suppressed. The location indicates a location of the patient device 170 (e.g., in a particular patient area 180, with a particular patient 182, and/or the like). A patient area record 280 may include, but is not limited to: identifier(s) of the patient area 180 (e.g., room number), and the like. A patient area record 280 may reference patient device records 270 corresponding to patient devices 170 deployed therein. A patient area record 280 may further include references to patient records 282 of patients 182 currently in the patient area 180. A patient record 282 may comprise patient identifier(s), patient condition data (described in further detail herein), and so on. A patient record 282 may include a reference to a patient area record 280 of the patient area 180 in which the patient 182 is being treated and/or may reference patient device records 270 of patient device(s) 170 being used to provide healthcare services to the patient 182.

Referring back to the responder record 136 of FIG. 2, the alarm assignment data 231 may further indicate a priority and/or preference for selection of the responder record 136 for a particular alarm notification 132. In some embodiments, a responder record 136 may be designated as a top-priority responder 153 (e.g., primary responder 153) for a particular set or type of alarm notifications 132, and may be designated as a lower-priority responder 153 (e.g., secondary, backup) for another set or type of alarm notifications 132. By way of example, a responder record 136 may be designated as a primary responder 153 for alarm notifications 132 pertaining to: particular patient area(s) 180 (e.g., a room, section, recovery area, and/or the like); particular patient(s) 182; a particular set of patient device(s) 170; and/or the like. The responder record 136 may be assigned secondary responsibility for alarm notifications 132 pertaining to nearby patient area(s) 180, patient(s) 182, and/or patient devices 170, and may have lower-priority responsibility for other alarm notifications 132.

The responder data 232 may comprise information pertaining to the particular responder 153, such as the types of alarm conditions the responder 153 is capable of resolving, a practice specialty, certification(s), a role of the responder 153 (e.g., specialist, primary care physician, physician's assistant, nurse, therapist, physiatrist, pharmacist, councilor, technician), and/or the like. In one embodiment, the responder data 232 of a responder record 136N may indicate that the responder 153 is a pharmacist who is certified to respond to alarm conditions pertaining to replenishment of closely controlled pain medication, whereas responder data 232 of another responder record 136A may indicate that the responder 153 is not certified to respond to such alarm conditions. Responder data 232 may further comprise information pertaining to practice specialties, which may be used to route alarm notifications 132 to appropriate personnel. In one embodiment, a responder record 136A may indicate that the responder 153 has extensive experience handling a particular type of heart condition; alarm notifications 132 pertaining to such heart conditions may be routed to the responder 153 in lieu of other responders 153 who may not have a similar level of experience (as indicated by respective responder data 232 of the respective responder records 136).

Security data 233 of a responder record 136 may comprise data to authenticate the identity of a responder 153, such as a password, password hash, public/private key pair, cryptographic signature, third-party authentication credential, and/or the like. The security data 233 may further comprise and/or correspond to security data of computing device(s) 155 registered to the responder 153, which may include a computing device 155 that the responder 153 has authorized to receive alarm notifications 132 directed thereto. The security data 233 may further include security data pertaining to particular messaging systems 101B that the responder 153 has authorized to receive alarm notifications 132.

The contact record data 234 may comprise data pertaining to communication mechanisms through which the responder 153 is registered to receive alarm notifications 132. The contact record data 234 may reference and/or link one or more contact records 138. The contact record data 234 may further comprise preferences of the responder 153 regarding the contact records 138 (e.g., specify preferred contact mechanisms). As used herein a "contact record" 138 refers to electronic data pertaining to a communication endpoint at which a responder 153 is registered to receive alarm notifications 132. A contact record 138 may comprise information pertaining to a particular computing device 155 registered to the responder 153. The computing device 155 may comprise a personal computing device of the responder 153; a computing device of a healthcare facility, such as a terminal on a network (e.g., internal network 101C and/or patient device network 101N); a dedicated terminal (described in further detail herein); and/or the like. Alternatively, or in addition, a contact record 138 may correspond to a device-independent messaging system 101B, such as an instant messaging system, a text messaging system, a proprietary messaging system, and/or the like. As illustrated in FIG. 2, a contact record 138 may include, but is not limited to: address data 235, contact security data 236, availability status data 237, and so on. Address data 235 may comprise network addressing information pertaining to a particular contact mechanism, such as a computing device 155, and may include but is not limited to: a network address on one or more electronic communication networks 101A-N, an identifier corresponding to a particular messaging system (e.g., an instant messaging system handle, email address, text messaging number), and/or the like. The contact security data 236 may comprise data for authenticating the contact mechanism (e.g., authenticating a particular computing device 155) and, in particular, data for verifying that the responder 153 has authorized use of the particular contact mechanism to receive alarm notifications 132. The contact security data 236 may correspond to a unique device identifier, such as a machine identifier, hardware identifier, media access control (MAC) address, and/or the like. The contact security data 236 may further comprise data to authenticate a particular computing device 155, such a credential, public/private key pair, cryptographic signature, and/or the like.

The availability status data 237 may indicate the current availability of the responder 153 to receive alarm notifications 132 from the PD management system 110 through the communication mechanism of the contact record 138. The availability status data 237 may be used to, inter alia, distinguish computing devices 155 that are currently available to receive alarm notifications 132 from the PD management system 110 from computing devices 155 that are unavailable. As used herein, a computing device 155 that is "available" to receive an alarm notification 132 refers to a computing device 155 that is in communication with the communication layer 150 through one or more electronic communication networks 101A-N. A computing device 155 that is "unavailable" refers to a computing device 155 that is not in communication with the communication layer 150 (e.g., is off, is disconnected from electronic communication network(s), and/or the like). The availability status data 237 may further indicate a latency (e.g., latency to/from a computing device 155, latency of a particular messaging system 101B), may comprise security parameters pertaining to the contact mechanism (e.g., encryption level), and so on.

Although particular embodiments of data structures are described herein, the disclosure is not limited in this regard and could be implemented using any data types and/or data structures maintained in any data management, access, and/or storage format.

Referring back to FIG. 1, the alarm manager 130 may be configured to update the availability status data 237 of contact records 138 by use of the communication layer 150. The communication layer 150 may be configured to verify connectivity to responders 153 through the contact mechanisms registered thereto (e.g., through the communication mechanism(s) registered to the responder records 136 in the alarm routing data 135). Verifying connectivity to a responder 153 may include, but is not limited to: establishing a connection to a computing device 155 through one or more electronic communication networks 101A-N, establishing a heartbeat connection to the computing device 155, transmitting data to the computing device 155, verifying transmission of data to the computing device 155, receiving data from the computing device 155 (either receiving directly from the computing device 155, receiving an authentication credential of a responder 153 from the computing device 155, authenticating the responder 153 at the computing device 155, and/or the like). The alarm manager 130 may update the availability status data 237 for the contact records 138 based on responses (if any) received at the communication layer 150. The alarm manager 130 may update the availability status data 237 to indicate that a particular contact record 138 is unavailable in response to determining that the responder 153 is unreachable through the corresponding contact mechanism (e.g., computing device 155 and/or messaging system 101B). The alarm manager 130 may update the availability status data 237 to indicate that a particular contact record 138 is available in response to determining that the responder 153 is reachable through the corresponding contact mechanism (e.g., receiving an acknowledgement, reply, and/or authentication within a time threshold). The alarm manager 130 may use the communication layer 150 to monitor the contact mechanisms of contact records 138 to identify contact records 138 that become unavailable and/or available over time. The communication layer 150 may be configured to periodically verify availability of contact records 138 (according to a particular interval and/or at a particular frequency), may establish a continuous connection to computing device(s) 155 of the contact records 138, and/or the like. The communication layer 150 may inform the alarm manager 130 of changes to the availability of particular computing device(s) 155 and/or contact mechanisms, and in response, the alarm manager 130 may update the alarm routing data 135 accordingly.

The PD configuration manager 140 may configure the patient device 170 to, inter alia, suppress alarm outputs of the patient device 170. Suppressing an alarm output may include, but is not limited to, configuring the patient device 170 to silence an audible alarm of the patient device 170, reducing the volume of an audible alarm of the patient device 170, disabling a visual alarm of the patient device 170, reducing the brightness of a visual alarm of the patient device 170, suppressing a haptic feedback alarm of the patient device 170, and/or the like. The PD configuration manager 140 may configure the patient device 170 by use of the PD integration module 120, as disclosed above. The PD configuration manager 140 may configure the patient device 170 to suppress alarm output in response to determining that one or more responders 153 are available to receive alarm notifications 132 from the PD management system 110. Determining that responders 153 are available to receive alarm notifications 132 may comprise (a) accessing alarm routing data 135 to identify responders 153 assigned to receive alarm notifications 132 corresponding to the patient device 170, and (b) determining whether the identified responders 153 are available through one or more contact mechanisms registered to identified responders 153 (e.g., based on availability status data 237 of contact records 138 registered to the identified responder records 136). The PD configuration manager 140 may reconfigure the patient device 170 to enable the alarm outputs thereof in response to determining that there are no responders 153 available to receive alarm notifications 132 from the PD management system 110, and/or responders 153 have failed to acknowledge and/or respond to alarm notifications 132 from the PD management system 110 within a time threshold.

In some embodiments, the PD configuration manager 140 is embodied as machine-executable instructions stored on non-transitory storage resources 115 of the computing device 111. Alternatively, or in addition, the PD configuration manager 140 may comprise hardware components, such as a processor, a circuit, programmable logic, and/or the like.

The PD integration module 120 may be configured to monitor the patient device 170 in order to, inter alia, identify alarm conditions detected by the patient device 170. The alarm condition may be detected by the patient device 170 even though the corresponding alarm output of the patient device 170 has been suppressed, as disclosed above. In response to identifying detection of an alarm condition by the patient device 170, the alarm manager 130 may be configured to select a computing device 155 to receive an alarm notification 132. As used herein, selecting a computing device 155 refers to selecting a particular computing device 155 of the responder 153 and/or selecting a computing device 155 corresponding to a messaging system through which the responder 153 is available to receive alarm notifications 132. The alarm manager 130 may be configured to select the computing device 155 to receive the alarm notification 132 from a plurality of registered computing devices 155, each registered computing device 155 and/or contact mechanism associated with a responder 153 designated to receive alarms of particular patient device(s) 170, patient area(s) 180, and/or patient(s) 182.

In some embodiments, the alarm manager 130 is configured to select the computing device 155 to receive the alarm notification 132 using the alarm routing data 135. Selecting may comprise: (a) identifying responder records 136 of responders 153 that are designated to receive the alarm notification 132 (e.g., based on alarm assignment data 231 and/or responder data 232 of the responder records 136), and (b) selecting contact record(s) 138 registered to the identified responder records 136 through which the responder 153 is available to receive alarm notifications 132 (e.g., based on availability status data 237 of the contact records 138).

The alarm manager 130 may be further configured to generate the alarm notification 132, and to instruct the communication layer 150 to send the alarm notification 132 to the selected computing device 155 via one or more electronic communication network(s) 101. The communication layer 150 may be configured to verify receipt of the alarm notification 132 by the responder 153 at the selected computing device 155. Verifying receipt of the alarm notification 132 may comprise receiving verification data from the selected computing device 155. Verifying receipt of the alarm notification 132 may further comprise authenticating a credential in the verification data, the credential authenticating the responder 153 and/or selected computing device 155 using, inter alia, security data and/or device security data, as disclosed herein.

Figure 3:
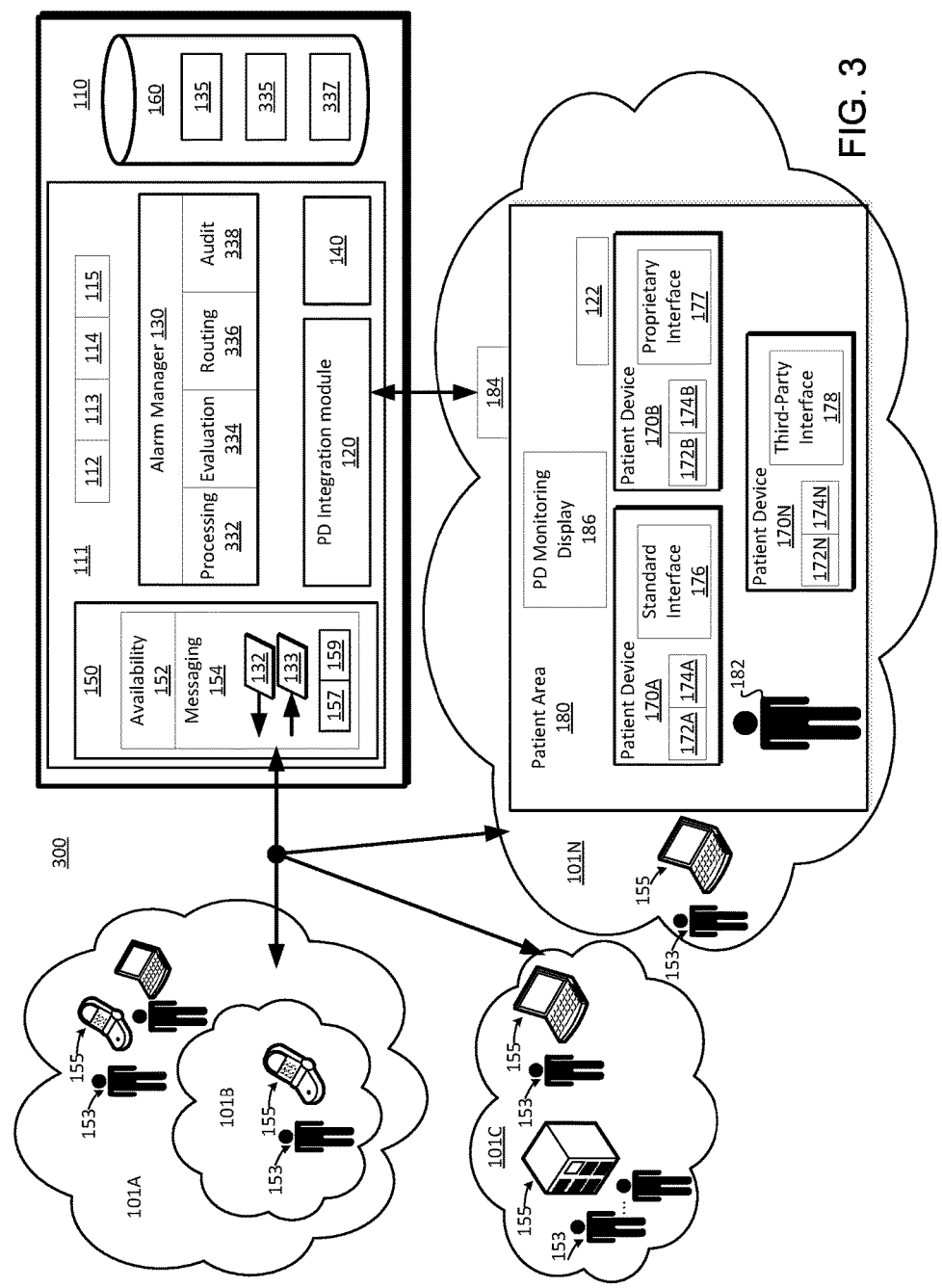
FIG. 3 is a block diagram of another embodiment of a system comprising a patient device management system.

FIG. 3 is a schematic block diagram of another embodiment of a system 300 comprising a PD management system 110. As depicted in the FIG. 3 embodiment, a patient area 180 may comprise a plurality of patient devices 170A-N providing healthcare services to a patient 182. The patient devices 170A-N may comprise respective input/output components 174A-N. As used herein, an input/output component 174A-N refers to a device, element, and/or interface for interacting with a patient device 170A-N. An input/output component 174A-N may include, but is not limited to: an input component, such as a keyboard, a pointing device, a mouse, a touch input device, a touch screen, a physical input device (e.g., a button, slider, and/or the like), a remote control device, a network input device, and/or the like; and an output component, such as a visual output device, a display, a display device, a display screen, a text output device, a printer, an audio output device, a speaker, a haptic feedback device, and/or the like. For example, the input/output components 174A-N of a patient device 170A-N may include a display screen, input components, audio outputs, and/or the like. Alternatively, an input/output component 174A-N of a patient device 170A-N may be embodied as a separate, independent device that is communicatively coupled to the patient device 170A-N through, inter alia, an electronic communication network (e.g., patient device network 101N). Such input/output components 174A-N may include, but are not limited to: a monitoring system, a monitoring computing device, a monitoring interface, a remote monitoring interface, a computing device, a personal computer, a mobile computing device, a tablet computing device, a personal digital assistant, and/or the like.

As illustrated in FIG. 3, patient devices 170A-N may comprise respective operating state data (state data 172A-N). As used herein, "operating state data" or "state data" refers to electronic data pertaining to the operation, status, and/or configuration of a patient device 170A-N. Accordingly, the state data 172A-N of a patient device 170A-N may include, but is not limited to, data pertaining to: a monitoring function of the patient device 170A-N, a healthcare function of the patient device 170A-N, a status of the patient device 170A-N, a configuration of the patient device 170A-N, and/or the like. The state data 172A-N of a patient device 170A-N may comprise electronic data stored in an electronic memory. Alternatively, or in addition, the state data 172A-N of a patient device 170A-N may be embodied as electronic data and/or data structures stored in non-transitory electronic storage (e.g., on a non-transitory storage medium). A patient device 170A-N may be configured to capture and/or maintain portions of the state data 172A-N in a memory of the patient device 170A-N. Alternatively, or in addition, portions of the state data 172A-N of a patient device may be captured and/or maintained by a separate computing device (e.g., in a patient device record 270).

The state data 172A-N of the patient device(s) 170A-N depicted in FIG. 3 may comprise patient monitoring information (e.g., current patient heart rate captured by a heart rate monitoring device), past patient monitoring information (e.g., a history of patient heart rate values captured by the heart rate monitoring device), monitoring configuration (e.g., how often monitoring is performed, alarm thresholds, and so on), configuration information relating to a healthcare function (e.g., a rate of drug delivery, how often a patient is allowed to dispense drugs, and so on), status (e.g., amount of medication remaining for medication delivery), an alarm output configuration of the patient device 170A-N, a status output configuration of the patient device 170A-N, and/or the like.

The patient devices 170A-N of FIG. 3 may be configured to detect alarm condition(s) in response to certain events and/or triggers. For example, a patient device 170A-N may perform a blood pressure monitoring function, and may detect an alarm condition in response to measuring a blood pressure value that is lower than a threshold. Another patient device 170A-N may be configured to provide drug delivery services, and may be configured to detect an alarm condition in response to an amount of remaining medication falling below a threshold. The patient devices 170A-N may be configured to generate outputs through, inter alia, input/output components 174A-N. In some embodiments, a patient device 170A-N may be configured to activate an alarm output in response to detecting an alarm condition. Alarm outputs of the patient device(s) 170A-N may be suppressed by, inter alia, modifying the configuration of the patient device(s) 170A-N, as disclosed herein.

The PD integration module 120 may be configured to interface with patient devices 170A-N, as disclosed herein. The PD integration module 120 may be configured to interface with different types of patient devices 170A-N having different interface mechanisms and/or protocols. As depicted in FIG. 3, the patient device 170A may comprise a standard interface 176, the patient device 170B may comprise a proprietary interface 177, and the patient device 170N may comprise a third-party interface 178. A standard interface 176 may comprise an interface that complies with one or more standards. A proprietary interface 177 may comprise an interface that is proprietary to a particular device and/or device manufacturer. A third-party interface 178 may comprise an integration component that is separate from the patient device 170N. The patient device 170N may, for example, comprise limited interface functionality and/or a proprietary interface, and the third-party interface 178 may provide additional interface functionality and/or a different interface (e.g., a standardized interface) to the patient device 170N. The patient integration module 120 may be configured to interface with the patient devices 170A-N through the respective interfaces 176, 177, and/or 178 thereof.

In some embodiments, the PD integration module 120 is communicatively coupled to patient device(s) 170A-N through an electronic communication network, such as the patient device network 101N. The disclosure is not limited in this regard, however, and could be adapted to integrate patient devices 170A-N on any suitable electronic communication network (e.g., an internal network 101C, an external network 101A, and/or the like). The PD integration module 120 may comprise network interface hardware, driver(s), protocol stack(s), and/or framework(s) to interface with patient devices 170A-N through the patient device network 101N. The standard interface 176 of the patient device 170A may comply with a particular standard, specification, framework, and/or protocol, such as the standards promulgated by the Health Level Seven International organization. The PD integration module 120 may comprise network link(s), interface(s), driver(s), protocol(s), and/or stack(s) to interface with the patient device 170A using the standard(s) implemented by the standard interface 176.

The PD integration module 120 may further comprise an PD interface device 122 to interface with the proprietary interface 177 of the patient device 170B. The integration device 122 may comprise link(s), interface(s), driver(s), protocol stack(s), and/or framework(s) to interface with the proprietary interface 177 of the patient device 170B. The PD interface device 122 may be further configured to interface with the patient device 170N through a third-party interface 178. In some embodiments, the PD interface device 122 comprises an interface, link, driver, protocol, and/or framework to communicatively couple the PD integration module 120 to a particular interconnect, bus, and/or interface of a patient device 170A-N, which may include, but is not limited to: a serial port; a Small Computer System Interface (SCSI) bus and/or interface; an IEEE 1394 (FireWire) interconnect and/or interface; a Fiber Channel interconnect and/or interface; a universal serial bus (USB) bus and/or interface; a proprietary interconnect, bus, and/or interface; a third-party interconnect, bus, and/or interface; and/or the like.

As disclosed above, the PD integration module 120 may be configured to monitor the patient devices 170A-N in order to, inter alia, respond to detection of alarm conditions by the patient devices 170A-N. In response to detecting an alarm condition at a patient device 170A-N, the alarm manager 130 may select a computing device 155 to receive a corresponding alarm notification 132, as disclosed above. The alarm manager 130 may comprise a processing module 332, an evaluation module 334, a routing module 336, and an audit module 338. The alarm manager 130, and/or the modules thereof, may be embodied as machine-executable instructions stored on non-transitory storage resources 115 of the computing device 111. Alternatively, or in addition, the alarm manager 130 and/or the modules thereof may comprise hardware components, such as a processor, a circuit, programmable logic, and/or the like.

The processing module 332 may be configured to process state data 172A-N acquired from the patient devices 170A-N by the PD integration module 120. The processing module 332 may be configured to, inter alia, convert, normalize, and/or translate the acquired data into a format usable by other components of the PD management system 110. The processing module 332 may be further configured to parse the data acquired from the patient devices 170A-N in order to, inter alia, identify alarm conditions detected at the patient devices 170A-N, determine information pertaining to detected alarm conditions (e.g., extract and/or parse state data 172A-N of the patient devices 170A-N), and so on.

The evaluation module 334 may be configured to generate alarm notifications 132 in response to detection of alarm conditions at the patient devices 170A-N. Generating an alarm notification 132 may comprise generating electronic data that, inter alia, describes the alarm condition, identifies the patient device 170A-N corresponding to the alarm condition, identifies the patient area 180 and/or patient 182 corresponding to the alarm condition, assigns a criticality level to the alarm condition, assigns a response type to the alarm condition, and so on. The evaluation module 334 may be further configured to buffer, delay, and/or combine alarm notifications 132 in accordance with the criticality levels and/or response types assigned thereto.

The evaluation module 334 may be configured to identify the patient device 170A-N corresponding to the alarm condition using, inter alia, an identifier of the patient device 170A-N acquired by the PD integration module 120. The identifier of the patient device 170A-N may be included in state data 172A-N acquired from the patient device 170A-N by the PD integration module 120. The evaluation module 334 may be configured to identify the patient area 180 and/or patient 182 corresponding to the detected alarm condition by, inter alia, matching the identifier of the patient device 170A-N to a patient device record 270, patient area record 280, and/or patient record 282, as disclosed herein. The evaluation module 334 may be configured to determine information identifying the condition and/or event that triggered detection of the alarm condition at the patient device 170A-N, which may be extracted and/or parsed from state data 172A-N acquired from the patient device 170A-N. Such information may include, but is not limited to: monitoring data that triggered the alarm condition (e.g., a blood pressure value below a threshold), status data that triggered the alarm condition (e.g., less than a threshold amount of remaining medication), and so on.

The evaluation module 334 may be further configured to assign a criticality level to alarm conditions. The criticality level assigned to an alarm condition may quantify a relative criticality of the alarm. Accordingly, the assigned criticality level may indicate the urgency of the response to the alarm condition and/or determine the response type required for the alarm condition. The evaluation module 334 may be configured to assign criticality levels according to a predetermined range of values. Assigning the criticality level to an alarm condition may comprise: (a) evaluating characteristics of the alarm condition, (b) evaluating characteristics of the patient 182, and/or (c) comparing characteristics of the alarm condition to the characteristics of the patient 182. Evaluating characteristics of the alarm condition may comprise matching particular alarm conditions and/or events to particular criticality levels based on, inter alia, rules, policies, heuristics, a mapping table, and/or the like, which may be embodied as alarm evaluation rules 337 maintained in machine-readable, non-transitory storage (e.g., storage resources 115 and/or storage system 160). The evaluation module 334 may assign criticality levels based on information from the patient device 170A-N (e.g., state data 172A-N acquired from the patient device 170A-N by the PD integration module 120). In some embodiments, the patient device 170A-N may indicate the severity of the alarm condition, which may be used as the basis for the criticality level assigned to the alarm condition by the evaluation module 334.

In some embodiments, assigning a criticality level to the alarm condition comprises evaluating characteristics of the patient 182. The characteristics of the patient 182 may be accessible in a patient record 282 of the patient 182 (e.g., in condition data of the patient record 282). The condition data may indicate an overall health condition of the patient 182, which may be used to determine a criticality level of alarm conditions pertaining to the patient 182. In one embodiment, the evaluation module 334 is configured to increase criticality levels for a patient 182 who is identified as "frail" and/or is in a weakened condition (e.g., is recovering from a surgical procedure).

The evaluation module 334 may be further configured to compare characteristics of the patient 182 to characteristics of the alarm condition. As described above, the characteristics of the alarm condition may comprise information pertaining to the condition and/or event that resulted in detection of the alarm condition at the patient device 170A-N (e.g., low blood pressure). The characteristics of the patient 182 may indicate specific health conditions of the patient 182 (e.g., information indicating that the patient 182 has heart disease, respiratory problems, and/or the like). Assigning the criticality level to the alarm notification 132 may comprise matching characteristics indicative of health condition(s) of the patient 182 to the alarm condition(s) pertaining to such health condition(s). For example, the evaluation module 334 may increase the criticality level assigned to an alarm condition related to elevated heart rate in response to determining that the patient 182 suffers from heart disease.

Assigning a criticality level to the alarm notification 132 may further comprise evaluating related alarm conditions (if any) pertaining to the patient device 170, the patient area 180, and/or patient 182. The evaluation module 334 may assign an increased criticality level to an alarm notification 132 in response to determining that the patient device 170A-N has detected multiple alarm conditions (e.g., multiple alarms from the patient device 170A-N). The evaluation module 334 may be further configured to increase the criticality level assigned to the alarm condition in response to determining that multiple alarm conditions have been detected by two or more of the patient devices 170A-N (e.g., alarm conditions have been detected by both a heart rate monitor and a respiration monitor).

In some embodiments, the evaluation module 334 is configured to combine alarm conditions from a patient area 180 and/or patient 182 in order to, inter alia, reduce the number of alarm notifications 132 sent to responders 153 from the PD management system 110. Accordingly, the evaluation module 334 may be configured to buffer and/or delay generation of alarm notifications 132. During buffering, alarm conditions pertaining to the same patient area 180 and/or patient 182 may be combined into a single alarm notification 132. The buffering and/or delay of alarm notifications 132 may be based, inter alia, on a criticality level assigned to the alarm conditions by the evaluation module 334. Alarm conditions assigned a criticality level that exceeds a threshold may be sent immediately, whereas alarm conditions assigned lower criticality levels may be buffered and/or delayed for longer periods of time.

The evaluation module 334 may be further configured to assign a response type to alarm conditions. As discussed above, the response type assigned to an alarm condition may indicate the type of responder 153 required to handle the alarm. The response type may indicate a role and/or certification required to respond to the alarm condition. For example, an alarm condition related to replenishment of pain medication may be assigned a "pharmacist" response type. The evaluation module 334 may assign response types to alarm conditions according to one or more rules, policies, heuristics, mapping tables, and/or the like, as disclosed above.

As disclosed above, alarm notifications 132 generated by the evaluation module 334 may comprise electronic data that describes the alarm condition, identifies the patient device 170A-N corresponding to the alarm condition, identifies the patient area 180 and/or patient 182 corresponding to the alarm condition, assigns a criticality level to the alarm condition, assigns a response type to the condition, and so on. The electronic data may comprise markup content configured for rendering and display by a computing device 155. The alarm notifications 132 may further comprise response instructions requesting one or more of verification of receipt of the alarm notification 132, acceptance of responsibility for the alarm condition, confirmation that the alarm condition has been resolved, and so on. The alarm notifications 132 generated by the evaluation module 334 may define interface components to provide the requested response(s), such as a "verify receipt" interface button, an "accept responsibility" button, and/or the like. The alarm notifications 132 may further include instructions to facilitate response, such as information specifying the location of the patient device 170A-N, the patient area 180, and/or the patient 182; information pertaining to the patient 182 (e.g., health condition); information pertaining to the alarm condition itself; instructions on how to resolve the alarm condition; and so on.

The routing module 336 may be configured to select responders 153 to receive alarm notifications 132 generated by the evaluation module 334. The routing module 336 may select responders 153 by use of alarm routing data 135, as disclosed above. The routing module 336 may be configured to identify a set of responders 153 that are designated to receive alarm notifications 132 pertaining to the particular patient devices 170A-N, patient area 180, and/or patient 182, and select responders 153 of the identified set that are available to receive alarm notifications 132 from the PD management system 110. The responders 153 designated to receive particular alarm notifications 132 may be identified by use of alarm assignment data 231 of the responder records 136, as disclosed above. The responders 153 that are available to receive alarm notifications 132 may be identified by use of the alarm assignment data 231 (e.g., scheduling information) and/or availability status data 237 of contact records 138 registered to the responder records 136 thereof.

The routing module 336 may be further configured to select responders 153 for alarm notifications based on relative priority defined by, inter alia, alarm assignment data 231 of the responder records 136. The routing module 336 may be configured to select responders 153 that are designated as primary for an alarm notification 132, over responders 153 that are designated as lower-priority (e.g., secondary, backup, or the like).

The routing module 336 may be further configured to select responders 153 based on the response type assigned to the alarm notifications 132. The routing module 336 may be configured to select a responder 153 for a particular alarm notification 132 by identifying, through responder records 136, responders 153 designated to receive the particular alarm notification 132 (per alarm assignment data 231), capable of providing the required response to the alarm (per responder data 232), and available to receive alarm notifications 132 (per availability status data 237).

The routing module 336 may be further configured to select responders 153 for alarm notifications 132 based on criticality levels assigned to the alarms. Selecting a responder 153 may comprise identifying, through responder records 136, responders 153 designated to receive the particular alarm notification 132 (per alarm assignment data 231), capable of responding to alarm notifications 132 of the assigned criticality level (per responder data 232), and available to receive alarm notifications 132 (per availability status data 237).

The routing module 336 may identify a plurality of responders 153 that are available to receive a particular alarm notification 132. In some embodiments, the routing module 336 may send the alarm notification 132 to a plurality of the identified responders 153. The number of responders 153 selected to receive an alarm notification 132 may be based on, inter alia, the criticality level and/or response type of the alarm notification 132. Alarm notifications 132 assigned a high criticality level may be sent to a larger set of responders 153 than alarm notifications 132 assigned lower criticality levels. In some embodiments, alarm condition(s) of an alarm notification 132 may be sent to multiple responders 153 in order to ensure that the required response can be implemented within a particular time period. In one embodiment, the routing module 336 may select two or more responders 153 to receive an alarm notification 132 in response to determining that the alarm notification 132 requires two or more different response types (e.g., response by a pharmacist and a physician).

The routing module 336 may select a subset of a plurality of responders 153 that are available to receive a particular alarm notification 132 based on preferences and/or weighting criteria. In some embodiments, the routing module 336 assigns a weight to each responder 153 available to receive an alarm notification 132 using data of the corresponding responder records 136. The weight may be assigned based on the alarm assignment data 231 (e.g., whether the responder 153 is designated as "primary," "secondary," and/or the like), responder data 232 (e.g., role, capabilities, and/or certifications, such as physician, pharmacist, nurse, etc.), criticality level assigned to the alarm notification 132, response type assigned to the alarm notification 132, and so on. In some embodiments, the routing module 336 is configured to match responders 153 with tasks of appropriate criticality and/or type (e.g., assigning nurses to less critical alarm notifications 132, assigning physicians to more critical alarm notifications 132, assigning specialists to highly critical alarm notifications 132 requiring a specialized response, and so on). In one embodiment, a responder record 136 may indicate that a responder 153 is capable of responding to highly critical alarm notifications 132. The alarm routing module 336 may be configured to prioritize the responder 153 for highly critical alarm notifications 132 and may assign a lower priority to the responder 153 for less critical alarm notifications 132. Similarly, a responder 153 who is designated to respond to lower-priority alarm notifications 132 (per responder data 232) may be highly weighted for lower-priority alarm notifications 132 and have a lower weighting for more critical alarm notifications 132.

The routing module 336 may be configured to select a subset of available responders 153 based on weight(s) assigned to the responder records 136 for the particular alarm notification 132 (e.g., selecting the top N weighted responder records 136). In another embodiment, the routing module 336 may be configured to form responder teams comprising responders 153 having different roles, to avoid overstaffing particular alarm notifications 132 (e.g., sending an alarm notification 132 to a nurse and a physician rather than two physicians).

The routing module 336 may be configured to send alarm notifications 132 to selected responders 153 by use of, inter alia, the communication layer 150. As disclosed above, the communication layer 150 may comprise an availability module 152 configured to, inter alia, monitor registered computing devices 155 and/or messaging systems to verify whether responders 153 are available to receive alarm notifications 132 from the PD management system 110. The availability module 152 may be configured to verify availability by one or more of: establishing connections to computing devices 155 through one or more electronic communication networks 101A-N, transmitting data to computing devices 155, verifying transmission of data to the computing devices 155, establishing a connection to a computing device 155 through one or more electronic communication networks 101A-N, establishing a heartbeat connection to the computing device 155, transmitting data to the computing device 155, verifying transmission of data to the computing device 155, receiving data from the computing device 155 (either receiving directly from the computing device 155, receiving an authentication credential of a responder 153 from the computing device 155, authenticating the responder 153 at the computing device 155, and/or the like). The communication layer 150 may be further configured to update availability status data 237 of contact records 138 in accordance with responder messages 133 (if any) received in response to the operations disclosed above. The communication layer 150 may be further configured to update availability status data 237 to indicate a response time of responders 153 through various communication mechanisms (e.g., contact records 138), preference of the responders 153 for use of various communication mechanisms, last known contact time through various communication mechanisms, and so on.

The communication layer 150 may comprise a messaging service 154 configured to transmit alarm notifications 132 to a responder 153 in accordance with contact record(s) 138 of the corresponding responder record 136, receive responder messages 133 from responders 153, and so on. The messaging service 154 may be configured to transmit an alarm notification 132 to a responder 153 by one or more of: transmitting data to one or more computing devices 155 registered to the responder 153 through one or more electronic communication networks 101A-N; establishing a network connection with the one or more computing devices 155 registered to the responder 153; sending data to the responder 153 through one or more messaging systems 101B; pushing data to one or more computing devices 155 registered to the responder 153; responding to polling messages from computing device(s) 155 registered to the responder 153 (e.g., enabling computing device(s) 155 registered to the responder 153 to pull data from the PD management system 110); and so on. The messaging service 154 may be further configured to receive responder messages 133 from responders 153 through one or more electronic communication networks 101A-N by one or more of: receiving data from a computing device 155 registered to the responder 153 through one or more electronic communication networks 101A-N; establishing a network connection with a computing device 155 registered to the responder 153; receiving data from the responder 153 through a messaging system 101B; receiving data pushed to the PD management system 110 from a computing device 155 registered to the responder 153; receiving a polling message from a computing device 155 registered to the responder 153; and so on. In some embodiments, a responder record 136 may be associated with a plurality of different contact records 138. The communication layer 150 may be configured to transmit alarm notifications 132 to the corresponding responder 153 by, inter alia, sending the alarm notification 132 based on each contact record 138. Alternatively, the communication layer 150 may transmit alarm notifications 132 to the responder 153 according to preferences of the responder 153 (e.g., per the contact record data 234 of the responder record 136). The messaging service 154 may detect responder messages 133 from responders 153 and update the alarm manager 130 accordingly.

The alarm manager 130 may be configured to track the status of alarm notifications 132 after the alarm notifications 132 are sent to the responders 153 by the communication layer 150. The alarm manager 130 may track verification of receipt of alarm notifications 132, acceptance of responsibility for alarm notifications 132, resolution of alarm conditions, and so on. The alarm manager 130 may detect an alarm notification failure condition in response to one or more of: failing to receive verification of receipt of an alarm notification 132 within a receipt verification threshold, failing to receive acceptance of responsibility for an alarm notification 132 within an acceptance threshold, failing to receive confirmation that the alarm condition was resolved within a resolution threshold, and/or determining that the alarm condition persists at the patient device 170A-N after an alarm duration threshold. The receipt verification threshold, acceptance threshold, resolution threshold, and/or alarm duration threshold may be set in accordance with the criticality level and/or response type assigned to the alarm notification 132. Alarm notifications 132 assigned higher criticality levels may use shorter thresholds, and alarm notifications 132 of particular types (e.g., medication refill) may require response within a particular time period.

In response to detecting a response failure condition, the alarm manager 130 may be configured to reissue the alarm notification 132 to a different set of responders 153, activate an alarm device 184, and/or activate an alarm of one or more of the patient devices 170A-N. Reissuing the alarm notification 132 may comprise resending the alarm notification 132, sending the alarm notification 132 to different computing device(s) 155 and/or messaging systems, selecting different responders 153 for the alarm notification 132, and/or the like. In some embodiments, reissuing an alarm notification 132 comprises generating a new alarm notification 132 by use of the evaluation module 334 and/or selecting recipients for the new alarm notification 132 by use of the routing module 336. The evaluation module 334 may be configured to increase a criticality level of the new alarm notification 132. The routing module 336 may select different responders 153 for the new alarm notification 132 and/or select different computing device(s) 155 to which to send the new alarm notification 132.

In some embodiments, in response to detecting a response failure condition, the alarm manager 130 may activate an alarm device 184. The alarm device 184 may be separate from and/or independent of the patient devices 170A-N. The alarm device 184 may be located away from the patient 182 to avoid disturbing the patient 182 when activated. In some embodiments, the alarm device 184 is placed outside of a patient room. Alternatively, or in addition, the alarm device 184 may be placed at a centralized location within a healthcare facility (e.g., at a nurses station).

Alternatively or in addition, the alarm manager 130 may be configured to update a PD monitoring display 186 with information pertaining to the alarm notification 132, including alarm notification failure conditions. The PD monitoring display 186 may comprise information acquired from the patient devices 170A-N (e.g., state data 172A-N). The PD monitoring display 186 may comprise a summary of the operating state of a plurality of patient devices 170A-N. Accordingly, the PD monitoring display 186 may be configured to aggregate and/or combine information pertaining to the patient devices 170A-N into a single display interface. The PD monitoring display 186 may acquire state data 172A-N from the PD management system 110 (e.g., acquired by the PD integration module 120, as disclosed herein). The PD monitoring display 186 may include information pertaining to alarm conditions of the patient devices 170A-N. The PD monitoring display 186 may indicate that an alarm condition has been detected at a patient device 170A-N, indicate that an alarm notification 132 has been sent to one or more responders 153, and indicate a status of the alarm notification 132 (e.g., whether receipt has been verified, whether responsibility for the alarm notification 132 has been accepted, and so on). The PD monitoring display 186 may be further configured to activate one or more alarm outputs in response to the alarm manager 130 detecting an alarm notification failure condition, as disclosed above. The PD monitoring display 186 may comprise an independent computing device communicatively coupled to the PD management system 110 through one or more electronic communication network(s). The PD monitoring display 186 may receive display data pertaining to the patient devices 170A-N and/or alarm notification 132 from the communication layer 150 of the PD management system 110 (e.g., a web server of the communication layer 150). The PD monitoring display 186 may be placed away from the patient 182 to avoid disturbing the patient 182. In some embodiments, the PD monitoring display 186 is placed on an outside door of a patient room and/or located at a centralized location of a healthcare facility.

The alarm manager 130 may further comprise an audit module 338 configured to track the status of alarm notifications 132 and, in particular, to record auditing data 335 pertaining to alarm notifications 132. The auditing data 335 may comprise response statistics pertaining to alarm notifications 132, such as an elapsed time between detection of the alarm condition and selection of a responder 153, verification that the alarm notification 132 was received by the responder 153, acceptance of responsibility for the alarm condition by a responder 153, resolution of the alarm condition, and so on. The audit module 338 may record information pertaining to the alarm notification 132 transmitted to responders 153 by the communication layer 150, information pertaining to responses from responders 153 received via the communication layer 150, status of patient devices 170A-N, and so on.

Figure 4:
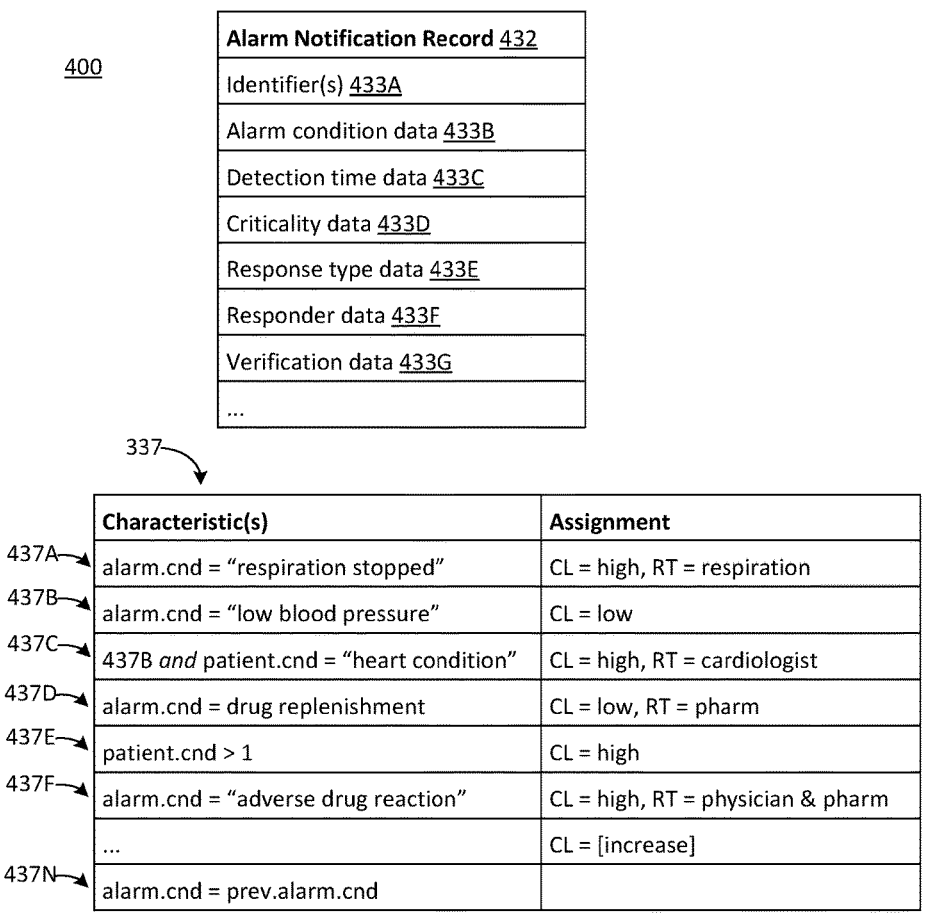
FIG. 4 depicts embodiments of an alarm notification record and alarm notification rules.

As disclosed above, the alarm manager 130 may be configured to acquire data pertaining to patient devices 170A-N by use of the PD integration module 120, process the data by use of the processing module 332, evaluate alarm conditions and generate corresponding alarm notifications 132 using the evaluation module 334, route alarm notifications 132 to responders 153 using the routing module 336, and audit responses to alarm notifications 132 by use of the audit module 338. FIG. 4 depicts embodiments of alarm management data structures 400 of the PD management system 110, including embodiments of an alarm notification record 432 and alarm notification rules 337.

An alarm notification record 432 may comprise information pertaining to alarm notifications 132 generated by the alarm manager 130 in response to detection of alarm conditions at the respective patient devices 170A-N. An alarm notification record 432 may comprise structured electronic data representing an alarm notification 132 in one or more of electronic memory, non-transitory storage, network transmission, and/or the like. An alarm notification record 432 may include, but is not limited to: identifier(s) 433A of the alarm notification 132, alarm condition data 433B, detection time data 433C, criticality data 433D, response type data 433E, responder data 433F, verification data 433G, and so on. The identifiers 433A may comprise any identifier of the alarm notification 132 (e.g., a unique identifier), an identifier of the patient device 170A-N, an identifier of a patient area 180, an identifier of a patient 182, and/or the like. Identifier(s) 433A for the patient device 170A-N, patient area 180, and/or patient 182 may reference a patient device record 270, a patient area record 280, and/or patient record 282, as disclosed herein. The alarm condition data 433B may comprise information pertaining to the alarm condition detected at the patient device 170A-N, and may include, but is not limited to: a description of the alarm condition, state data 172A-N from the patient device 170A-N, measurement data corresponding to the alarm condition (e.g., blood pressure measurements that triggered a low blood pressure alarm), status data corresponding to the alarm condition (e.g., amount of medication available to be dispensed), and so on. The detection time data 433C may indicate a time at which the alarm condition was detected at the patient device 170A-N. The detection time data 433C may correspond to a time stamp maintained in state data 172A-N of the patient device 170A-N and/or a time stamp corresponding to a time that the PD integration module 120 determined that the alarm condition had been detected at the patient device 170A-N (e.g., may indicate a lag time, if any, between detection of the alarm condition at the patient device 170A-N, and detection of the alarm condition by the PD management system 110). The criticality data 433D may specify the criticality level assigned to the alarm notification 132. The criticality data 433D may comprise a discrete criticality value (e.g., high, low, etc.), may comprise a value in a particular range, and/or the like. The response type data 433E may indicate one or more response types assigned to the alarm notification 132. As disclosed herein, a "response type" of an alarm notification 132 may identify the type of action(s) required to respond to the alarm condition detected at the patient device 170A-N. The responder data 433F may identify responders 153 selected to receive the alarm notification 132. The responder data 433F may reference and/or link to responder records 136 and/or contact records 138 of responders 153 selected to respond to the alarm condition. The responder data 433F may further comprise weights and/or preferences for the respective responders 153, may comprise data pertaining to alarm notifications 132 transmitted to the responders 153, and so on. The verification data 433G may comprise data pertaining to responder message(s) 133 from the selected responders 153, such as times at which receipt, acknowledgement, acceptance, and/or completion of the alarm messages occurred. The verification data 433G may further comprise response time thresholds assigned to the alarm notification 132, whether alarm notifications 132 were sent to additional backup responders 153, and so on.

The alarm condition data 433B may be derived from state data 172A-N acquired from the patient device 170A-N and processed by the processing module 332, as disclosed herein. The evaluation module 334 may use alarm condition data 433B to assign criticality data 433D and/or response type data 433E to the alarm notification record 432. The evaluation module 334 may determine criticality data 433D for an alarm notification record 432 by, inter alia, evaluating alarm notification rules 337, which may be defined as machine-readable instructions stored on non-transitory storage (e.g., storage resources 115 and/or storage system 160). Exemplary embodiments of alarm notification rules 337 are depicted in FIG. 4. The evaluation module 334 may assign criticality level(s) and/or response type(s) to alarm notifications 132 using alarm notification rules 337. As illustrated in FIG. 4, alarm notification rules 337 may, inter alia, assign characteristics of alarm conditions, characteristics of the patient 182, and so on, to respective criticality and/or response types. The alarm notification rule 437A assigns a high criticality level and "respiration" specialist response type in response to alarm characteristics ("alarm.cnd") indicating that patient respiration has stopped. The alarm notification rule 437B assigns a low criticality level and no specific response type requirement to an alarm pertaining to low blood pressure. The alarm notification rule 437C compares characteristics of the patient 180 to characteristics of the alarm condition to assign a high criticality level and "cardiologist" response type to the "low blood pressure" alarm condition if the patient characteristics indicate that the patient 180 is suffering from a heart condition. The alarm notification rule 437D assigns a low criticality level and response type of "pharmacist" to a drug replenishment alarm condition. Another rule (not shown) may assign an increased criticality level if characteristics of the alarm condition and/or patient 180 indicate that the drug is particularly critical to the health condition of the patient 180. As disclosed above, alarm criticality and/or response type may be based on whether the patient 180 is subject to multiple alarm conditions. The alarm notification rule 437E increases the criticality level assigned to an alarm notification 132 in response to determining that the patient 180 is subject to multiple alarm conditions (e.g., more than one alarm condition by a particular patient device 170A-N and/or multiple different patient devices 170A-N). The alarm notification rule 437F may incorporate one or more alarm characteristics to determine that the alarms correspond to an "adverse drug reaction" by the patient 182. The determination of rule 437F may be based on alarm conditions of one or more patient devices 170A-N (e.g., alarms from monitoring devices in combination with state data 172A-N indicating administration of a particular drug to the patient 180). The rule 437F may assign a high criticality level to the "adverse drug reaction" alarm characteristics, and may assign a response type to include both a "physician" and "pharmacist." The alarm notification rule 437N may be based on a history of alarms pertaining to the patient 182 and may increase the alarm criticality assigned to the alarm notification 132 in response to identifying one or more other alarm conditions pertaining to the patient 182 within a time threshold. Although particular embodiments of alarm notification rules 337 are described herein, the disclosure is not limited in this regard, and could be adapted to incorporate rules, policies, heuristics, expert systems, and/or any other suitable mechanism for generating alarm notifications 132, assigning criticality levels to alarm notifications 132, assigning response types to alarm notifications 132, and so on.

The routing module 336 may use data of an alarm notification record 432 populated by the processing module 332 and/or evaluation module 334 to select responders 153 to receive the corresponding alarm notification 132. As disclosed above, the routing module 336 may be configured to identify responder records 136 of responders 153 that are designated to receive and respond to alarms of particular patient devices 170A-N, patient area(s) 180, and/or patients 182, by matching the identifier(s) 433A and/or alarm condition data 433B to the alarm assignment data 231 of the responder records 136. The routing module 336 may be further configured to select responder records 136 based on criticality data 433D and/or response type data 433E by, inter alia, matching responder data 232 of the responder records 136. The routing module 336 may update responder data 433F of the alarm notification record 432 to identify the responder(s) 153 selected to receive the alarm notification 132 and/or identify the contact records 138 to use to send the alarm notification 132. The responders 153 included in the responder data 433F may be ordered and/or weighted by preference, as disclosed herein. In some embodiments, the responder data 433F may include a set of one or more primary responders 153, a set of one or more secondary responders 153, and so on. Routing module 336 may be configured to send the alarm notification 132 to the indicated primary responders 153, and to send the alarm notification 132 to the other, secondary responders 153 in the event of an alert notification failure condition, as disclosed herein.

The audit module 338 may be configured to update verification data 433G of the alarm notification record 432 in response to responder message(s) 133, and/or monitoring state data 172A-N of the patient devices 170A-N. Audit module 338 may record one or more verification time stamps at times when the communication layer 150 verified receipt, acceptance, and/or completion of the alarm notification 132. The audit module 338 may further be configured to record a time stamp indicating a time at which state data 172A-N of the patient device 170A-N indicated that the alarm condition of the alarm notification record 432 was cleared. The audit module 338 may store auditing data 338 on a machine-readable, non-transitory storage medium, such as the storage resources 115 of the computing device 111, the storage system 160, and/or the like. The auditing data 338 may comprise alert notification records 432, as disclosed herein.

Figure 5:
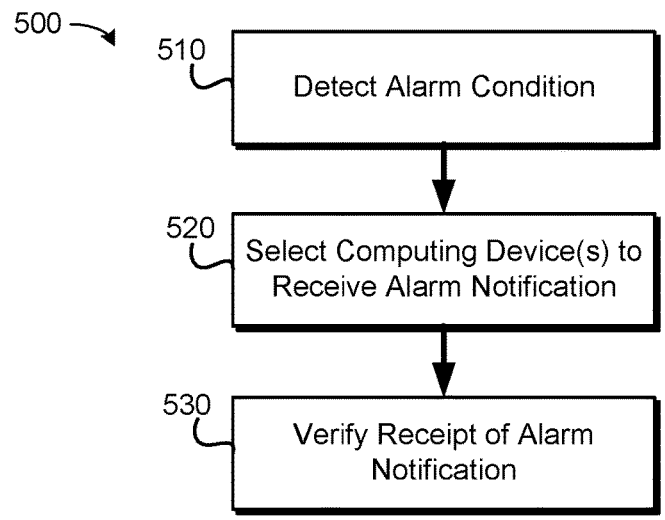
FIG. 5 is a flow diagram of one embodiment of a method for managing patient devices.

FIG. 5 is a flow diagram of one embodiment of a method 500 for managing patient devices 170A-N. The steps and/or operations of the method 500, and the other methods disclosed herein, may be implemented by use of hardware components, such as network link(s) and/or interfaces, processing resources 112, memory resources 113, communication resources 114, storage resources 115 and/or 160, and so on. Alternatively, or addition, portions of the methods disclosed herein may be embodied as executable instructions stored on a non-transitory storage medium.

Step 510 may comprise detecting an alarm condition at a patient device 170A-N. Step 510 may comprise monitoring patient devices 170A-N by use of a PD integration module 120, as disclosed herein. Step 510 may comprise acquiring state data 172A-N from patient devices 170A-N through one or more of a standard interface 176, a proprietary interface 177, a third-party interface 178, and/or the like. Step 510 may comprise determining detection of an alarm condition at the patient device 170A-N based on the acquired state data 172A-N. Alternatively, or in addition, step 510 may comprise detecting assertion of an alarm condition in the state data 172A-N, detecting assertion of an alarm output (e.g., an input/output component 174A-N of the patient device 170A-N), and/or the like. Step 510 may further comprise configuring the patient device 170A-N to silence and/or suppress one or more output components.

Step 520 may comprise selecting computing device(s) 155 to receive an alarm notification 132 corresponding to the detected alarm condition. Step 520 may comprise identifying responders 153 designated to receive the alarm notification 132 pertaining to the patient device 170A-N, the patient area 180, and/or the patient 182. Step 520 may comprise identifying responders 153 by use of routing data 135 (e.g., by evaluating alarm assignment data 231 of responder records 136 of the routing data 135). Step 520 may further comprise identifying responders 153 available to receive alarm notifications 153 (e.g., based on availability data 237 of contact records 138 registered to the identified responders 153).

In some embodiments, step 530 further comprises assigning a criticality level to the alarm notification 132 and/or assigning a response type to the alarm notification 132 (e.g., setting criticality data 433D and/or response type data 433E of the alarm notification record 432). Step 530 may comprise assigning a criticality level and/or response type based on, inter alia, characteristics of the alarm condition and/or characteristics of the patient 182. In some embodiments, step 530 comprises applying alarm evaluation rules 337, as disclosed herein. Step 520 may further comprise selecting responders 153 by comparing responder data 232 of the responder records 136 to the criticality level and/or response type assigned to the alarm notification 132. Step 520 may further comprise ordering and/or assigning relative weights to the responders 153, as disclosed herein.

Step 530 may comprise verifying receipt of the alarm notification 132 by the responders 153 identified at step 520. Step 530 may comprise transmitting the alarm notification 132 to computing devices 155 registered to the responders 153 by use of the communication layer 150 (via one or more electronic communication networks 101A-N). Step 530 may further comprise receiving a responder messages 133 indicating receipt of the alarm notification 132, accepting responsibility to respond to the alarm notification 132, confirming completion of the alarm notification 132, and so on. Step 530 may further include identifying a second, different set of responders 153 in response to an alarm notification failure condition (e.g., failure to receive a responder message 133 within a time threshold). In some embodiments, 530 further includes activating a dedicated alarm device 184 and/or PD monitoring display 186, as disclosed herein.

Figure 6:
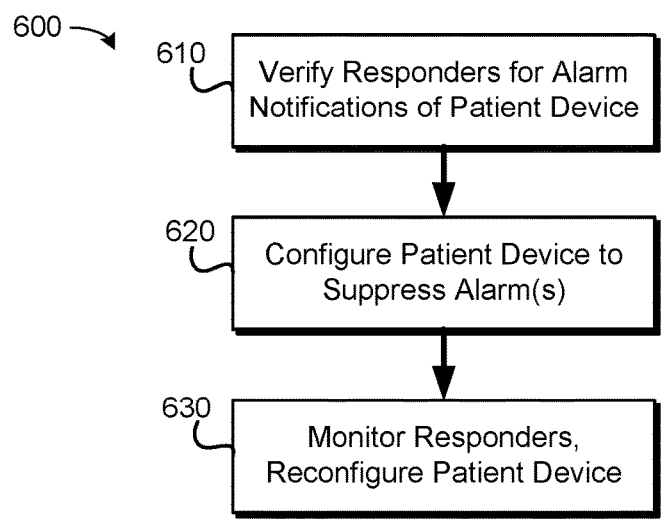
FIG. 6 is a flow diagram of another embodiment of a method for managing patient devices.

FIG. 6 is a flow diagram of another embodiment of a method 600 for managing patient devices. Step 610 may comprise verifying that responders 153 are available to receive alarm notifications 132 pertaining to a particular patient device 170A-N. Step 610 may comprise monitoring computing device(s) 155 registered to responders 153 designated to receive alarm notifications 132 pertaining to the patient device 170A-N (by use of the availability module 152 of the communication layer 150). Step 610 may comprise establishing a connection to a computing device 155 through one or more electronic communication networks 101A-N, establishing a heartbeat connection to the computing device 155, transmitting data to the computing device 155, verifying transmission of data to the computing device 155, receiving data from the computing device 155 (either receiving directly from the computing device 155, receiving an authentication credential of a responder 153 from the computing device 155, authenticating the responder 153 at the computing device 155, and/or the like). Step 610 may further comprise updating availability status data 237 of contact records 138 registered to respective responder records 136, as disclosed herein. Step 610 may further comprise verifying that the patient device 170A-N is communicatively coupled to the PD management system 110 (e.g., though the PD integration module 120). Step 610 may comprise confirming that the PD integration module 120 is able to access state data 172A-N of the patient device 170A-N and/or monitor detection of alarm conditions at the patient device 170A-N.

Step 620 may comprise configuring the patient device 170A-N to suppress and/or silence one or more input/output components 174A-N thereof. Step 620 may comprise configuring the patient device 170A-N to modify an alarm output (e.g., silence and/or reduce the volume of an audible alarm). Step 620 may further comprise configuring the patient device 170A-N to silence one or more status outputs (e.g., silence an audible "heartbeat" output).

Step 630 may comprise monitoring responders 153 designated to receive alarm notifications 132 pertaining to the patient device 170A-N. Step 630 may comprise verifying that the responders 153 are available to receive alarm notifications 132 pertaining to the patient device 170A-N. Step 630 may comprise periodically and/or continually verifying connectivity to the responders 153 by use of the communication layer 150, as disclosed herein. Step 630 may further comprise reconfiguring the patient device 170A-N to enable one or more of an alarm output and a status output in response to determining that responder 153 are not available to receive alarm notifications 132 pertaining to the patient device 170A-N. Alternatively, or in addition, step 630 may comprise configuring an alarm device 184 and/or PD monitoring display 186 to display status information and/or alarm notifications 132 pertaining to the patient device 170A-N.

Figure 7:
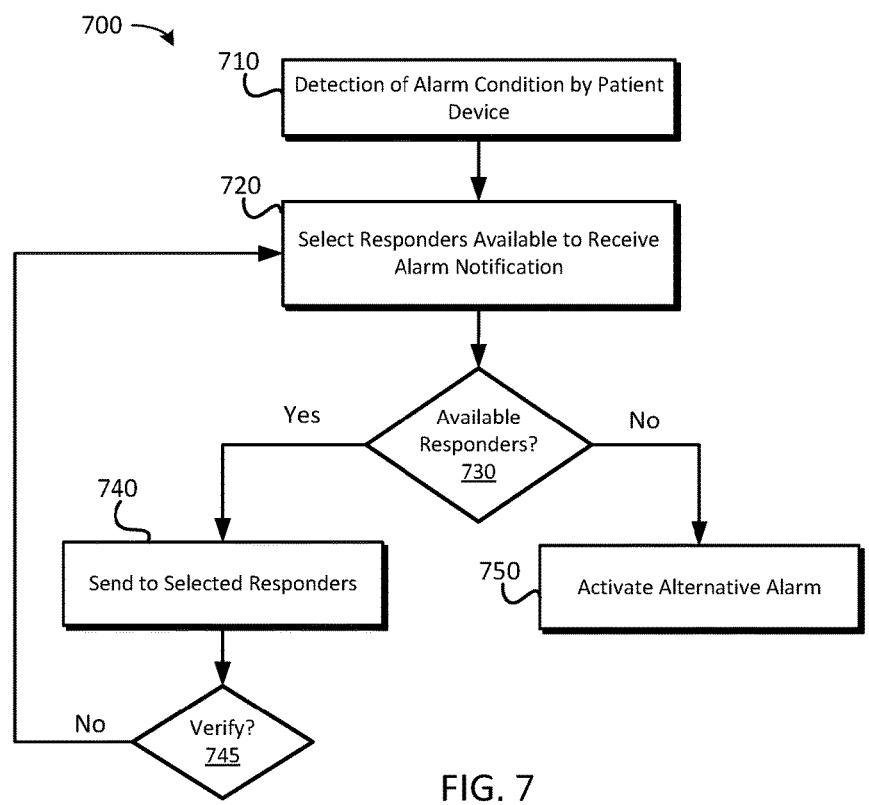
FIG. 7 is a flow diagram of another embodiment of a method for managing patient devices.

FIG. 7 is a flow diagram of another embodiment of a method 700 for managing patient devices. Step 710 comprises determining that a patient device 170A-N has detected an alarm condition, as disclosed herein. Step 720 may comprise selecting responders 153 to receive the alarm notification 132. Step 720 may comprise a) processing status data 172A-N and/or other information acquired from the patient device 170A-N, b) determining characteristics of the alarm condition, characteristics of the patient 182, and so on, to assign a criticality level and/or response type to the alarm notification 132 (e.g., applying alarm evaluation rules 337), c) using alarm routing data 135 to select responders 153 to receive the alarm notification 132 (e.g., by identifying responder records 136 designated to receive the alarm notification 132, matching the assigned criticality level and/or response type to responder data 232, selecting responders that are available to receive the alarm notification 132 based on alarm assignment data 231 and/or contact records 138 registered to the responders 153, and so on). Step 720 may further comprise setting one or more of a receipt verification threshold, acceptance threshold, resolution threshold, and/or alarm duration threshold for the alarm notification 132 based on, inter alia, the criticality and/or response type assigned to the alarm notification 132.

Step 730 may comprise determining whether responders 153 available to receive the alarm notification 132, as disclosed herein. Step 740 may comprise sending the alarm notification 132 to the selected responders 153 (e.g., by sending electronic data corresponding to the alarm notification 132 to computing devices 152 registered to the responders 153 via one or more electronic communication networks 101A-N). Step 745 may comprise verifying receipt, acknowledgement, acceptance, and/or completion of the alarm notification 132. Step 745 may comprise receiving responder messages 132 via one or more electronic communication networks 101A-N, monitoring the patient devices 170A-N that detected the alarm condition, and so on, as disclosed herein. Step 745 may comprise detecting an alarm notification failure condition in response to one or more of: failing to receive verification of receipt of an alarm notification 132 within a receipt verification threshold, failing to receive acceptance of responsibility for an alarm notification 132 within an acceptance threshold, failing to receive confirmation that the alarm condition was resolved within a resolution threshold, and/or determining that the alarm condition persists at the patient device 170A-N after an alarm duration threshold.

If an alarm notification failure condition is detected at step 745, the flow may continue at step 730 where another, different set of responders 153 are identified and the flow may continue as disclosed above by a) selecting the responders 153 at step 720, verifying that responders 153 are available at step 730, sending the alarm notification to the responders 153 at step 740, and verifying receipt, acknowledgement, acceptance, and/or completion of the alarm notification 132 at step 745.

If no other responders 153 are available (step 730), the flow may continue at step 750. Similarly, if another alarm notification failure condition occurs, and/or an attempt threshold is exceeded, the flow may continue to step 750. Step 750 may comprise activating one or more alternative alarms which may include, but is not limited to: configuring the patient device 170A-N to activate one or more alarm outputs thereof, activating an alarm device 184, activating an alarm output of the PD monitoring display 186, and/or the like.

Figure 8:
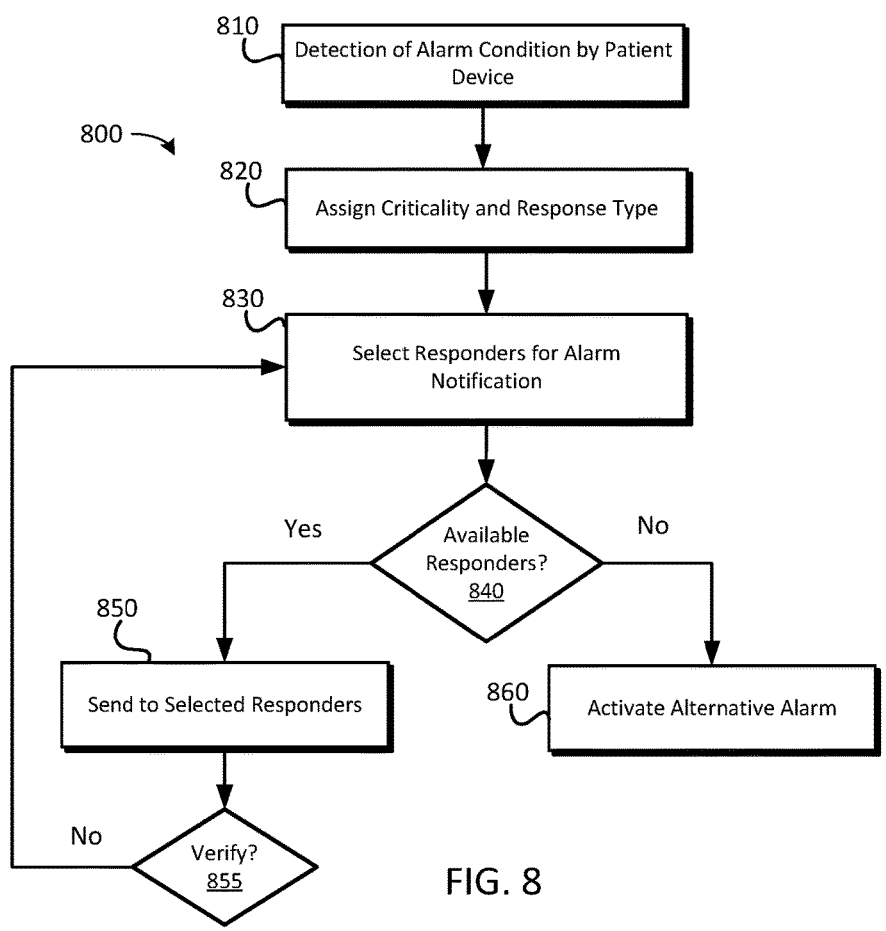
FIG. 8 is a flow diagram of another embodiment of a method for managing patient devices.

FIG. 8 is a flow diagram of another embodiment of a method 800 for managing patient devices. Step 810 may comprise detecting an alarm condition at a patient device 170A-N, as disclosed herein. Step 820 may comprise assigning a criticality and/or response type to the alarm notification, as disclosed herein. Step 820 may further comprise generating an alarm notification record 432 to represent the alarm notification 132. Step 820 may comprise populating the alarm notification record 432 by, inter alia, assigning identifier(s) 433A to the alarm notification record 432, setting alarm condition data 433B of the alarm notification record 432, setting detection time data 433C of the alarm notification record 432, assigning criticality data 433D to the alarm notification record 432, assigning response type data 433E to the alarm notification record 432, and so on. Assigning the criticality data 433D and/or response type data 433E may comprise applying alarm evaluation rules 337, as disclosed herein.

Step 830 may comprise selecting responders for 153 for the alarm by use of responder records 153, as disclosed herein. Step 830 may further comprise setting responder data 433F of the alarm notification record 432 specifying the selected responders 153 and/or contact records 138 at which the responders 153 are available to receive the alarm notification 132. Step 840 may comprise verifying that there are responders 153 available to receive the alarm notification 132. Step 850 may comprise sending alarm notifications 132 to the selected responders 153, and verifying receipt, acknowledgement, acceptance, and/or completion of the alarm notifications 132, as disclosed herein. Step 855 may comprise selecting another set of responders for the alarm notification 132 at step 830 in response to an alarm notification failure condition. Step 860 may comprise activating an alternative alarm in response to failure to verify receipt, acknowledgement, acceptance, and/or completion of the alarm notification 132. Step 830, 840, 850, 855, and 860 may further comprise updating responder data 433F and/or verification data 433G of the alarm notification record 432 in a persistent data store by use of the audit module 338, as disclosed herein.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system (e.g., one or more of the steps may be deleted, modified, or combined with other steps). Therefore, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Additionally, as will be appreciated by one of ordinary skill in the art, principles of the present disclosure may be reflected in a computer program product on a machine-readable storage medium having machine-readable program code means embodied in the storage medium. Any tangible, non-transitory machine-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a machine-readable memory that can direct a computer or other programmable data processing apparatus to function in a particular manner, such that the instructions stored in the machine-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components that are particularly adapted for a specific environment and operating requirements may be used without departing from the principles and scope of this disclosure. These and other changes or modifications are intended to be included within the scope of the present disclosure.

We claim:

1. A system, comprising:
an integration module configured to monitor a patient device for detection of an alarm condition at the patient device;
an alarm manager configured to select a computing device to receive an alarm notification pertaining to the detected alarm condition, wherein selecting the computing device comprises:
evaluating responder assignment data stored in a non-transitory data store to determine a responder to assign to the alarm notification,
selecting a first computing device based on alarm routing data pertaining to computing devices registered to the assigned responder, wherein the first computing device is selected in response to determining that the first computing device is available to receive the alarm notification for the assigned responder; and
a communication layer configured to verify receipt of the alarm notification by the assigned responder at the first computing device.

2. The system of claim 1, wherein the alarm manager is further configured to maintain the alarm routing data within the non-transitory data store, the alarm routing data comprising network address data of computing devices registered to respective responders of a plurality of responders and availability data pertaining to the registered computing devices, the availability data to distinguish registered computing devices that are available to receive alarm notifications via an electronic communication network from registered computing devices that are unavailable to receive alarm notifications via the electronic communication network, wherein to determine the availability data, the alarm manager is further configured to:
transmit availability requests to network addresses of respective registered computing devices, and
record availability data pertaining to the respective registered computing devices based on responses to the transmitted availability requests.

3. The system of claim 2, wherein recording the availability data pertaining to a registered computing device comprises one or more of:
recording that the registered computing device is unavailable to receive alarm notifications in response to failing to receive a response within a response time threshold,
recording that the registered computing device is available to receive alarm notifications in response to receiving a response within the response time threshold, and
recording that the registered computing device is available to receive alarm notifications for a particular responder in response to validating an authentication credential of the particular responder within the response time threshold.

4. The system of claim 2, wherein:
the alarm manager is further configured to register a first computing device to the assigned responder in the alarm routing data in response to verifying an authentication credential received from the first computing device through the electronic communication network, and
the first computing device is selected to receive the alarm notification in response to the alarm routing data indicating that the first computing device is available to receive the alarm notification.

5. The system of claim 1, wherein the alarm manager is further configured to transmit the alarm notification to the first computing device by use of the communication layer, and wherein the alarm notification comprises a request for one or more of: verification of receipt of the alarm notification, acceptance of responsibility for the alarm notification, and confirmation that the alarm condition of the alarm notification has been resolved.

6. The system of claim 1, wherein the alarm manager is further configured to send the alarm notification to a second computing device in response to one or more of:
determining that a message verifying receipt of the alarm notification has not been received by the communication layer within a receipt verification threshold,
determining that a message indicating acceptance of responsibility for the alarm notification has not been received by the communication layer within an acceptance threshold,
receiving a message rejecting acceptance of responsibility for the alarm notification,
determining that a message confirming resolution of the alarm notification has not been received within a resolution threshold, and
determining that a time elapsed since detection of the alarm condition at the patient device exceeds an alarm duration threshold.

7. A method, comprising:
monitoring a patient device to detect an alarm condition at the patient device;
selecting a responder to receive an alarm notification pertaining to the detected alarm condition, wherein selecting the responder comprises:
identifying one or more responders designated to receive alarm notifications pertaining to the patient device based on responder assignment data of a plurality of responders, and
selecting the responder from the one or more identified responders based on availability data pertaining to computing devices registered to the identified responders, the availability data indicating that a first computing device registered to the selected responder is available to receive alarm notifications through an electronic communication network;
transmitting the alarm notification to the first computing device through the electronic communication network; and
verifying receipt of the alarm notification by the selected responder at the first computing device.

8. The method of claim 7, further comprising maintaining alarm routing data on a non-transitory storage medium, the alarm routing data comprising network address data of computing devices registered to respective responders and availability data that distinguishes registered computing devices that are available to receive alarm notifications via the electronic communication network from registered computing devices that are unavailable to receive alarm notifications via the electronic communication network.

9. The method of claim 7, further comprising:
assigning a criticality level to the alarm notification, wherein assigning the criticality level comprises one or more of evaluating state data of the patient device pertaining to the detected alarm condition, identifying one or more other alarm conditions pertaining to a patient corresponding to the alarm condition, and matching a condition of a patient corresponding to the alarm condition to the detected alarm condition;

wherein the one or more responders are identified based on the assigned criticality level.

10. The method of claim 7, further comprising:
determining a response type for the alarm notification, wherein determining the response type comprises one or more of: matching an identifier of the patient device to one of a plurality of pre-defined response types, and applying evaluation rules to one or more of state data of the patient device, patient data of a patient associated with the detected alarm condition, and one or more other detected alarm conditions associated with the patient;
wherein the one or more responders are identified based on the determined response type.

11. The method of claim 7, further comprising:
assigning a criticality level and response type to the alarm notification based on data pertaining to one or more of the patient device and a patient associated with the patient device;
wherein identifying the one or more responders comprises identifying responders having responder assignment data matching the assigned criticality level and response type.

12. The method of claim 7, further comprising transmitting the alarm notification to a second computing device through the electronic communication network in response to one or more of:
failing to verify receipt of the alarm notification by the selected responder at the first computing device within a verification threshold,
the selected responder failing to accept responsibility for the alarm notification within an acceptance threshold,
the selected responder rejecting responsibility for the alarm notification,
the alarm notification not being resolved within a resolution threshold,
an elapsed time from detection of the alarm condition at the patent device exceeding an alarm duration threshold.

13. A non-transitory machine-readable storage medium comprising executable instructions configured to cause a computing device to perform operations, comprising:
generating an alarm notification record to represent an alarm condition detected at a patient device;
selecting a responder to receive the generated alarm notification, wherein selecting the responder comprises,
evaluating assignment data of responder records stored in a non-transitory data store to identify a set of one or more responder records that are assigned to receive the alarm notification, and
selecting a responder record from the identified set based on availability data of contact records registered to the responder records, the availability data identifying computing devices available to receive alarm notifications for specified responders through an electronic communication network;
transmitting electronic data of the alarm notification record to one or more computing devices registered to the selected responder through the electronic communication network; and
verifying receipt of the electronic data of the alarm notification record at one or more of the computing devices registered to the selected responder.

14. The non-transitory machine-readable storage medium of claim 13, the operations further comprising verifying availability of contact records registered to the responder records, wherein verifying availability of a contact record comprises one or more of:
receiving data from the computing device through the electronic communication network, and
authenticating a credential transmitted from the computing device through the electronic communication network.

15. The non-transitory machine-readable storage medium of claim 14, the operations further comprising configuring the patient device to silence an alarm output of the patient device in response to verifying availability of a contact record of a responder record having alarm assignment data corresponding to the patient device.

16. The non-transitory machine-readable storage medium of claim 13, the operations further comprising monitoring, the patient device to detect the alarm condition at the patient device.

17. The non-transitory machine-readable storage medium of claim 16, the operations further comprising monitoring the patient device through one or more of a standard interface of the patient device, a proprietary interface of the patient device, and a third-party interface of the patient device.

18. The non-transitory machine-readable storage medium of claim 13, the operations further comprising:
acquiring state data from the patient device; and
detecting the alarm condition at the patient device in response to acquiring the state data from the patient device.

19. The non-transitory machine-readable storage medium of claim 18, the operations further comprising:
transmitting electronic data of the alarm notification record to one or more computing devices registered to a responder other than the selected responder in response to one or more of:
determining that receipt of the electronic data of the alarm notification record by the selected responder has not been verified within a first time threshold,
determining that the selected responder has failed to accept responsibility for the alarm condition within a second time threshold,
determining that the selected responder has rejected responsibility for the alarm condition, and
determining that an elapsed time from detection of the alarm condition at the patent device exceeds a third time threshold.

20. The non-transitory machine-readable storage medium of claim 13, the operations further comprising suppressing a status output of the patient device in response to acquiring state data from the patient device.

* * * * *

UNITED STATES PATENT AND TRADEMARK OFFICE
CERTIFICATE OF CORRECTION

| | | |
|---|---|---|
| PATENT NO. | : 10,262,110 B2 | Page 1 of 1 |
| APPLICATION NO. | : 15/354724 | |
| DATED | : April 16, 2019 | |
| INVENTOR(S) | : Joseph Tonna et al. | |

It is certified that error appears in the above-identified patent and that said Letters Patent is hereby corrected as shown below:

On the Title Page

Item (72), add:
Brent Elieson, Salt Lake City, UT (US)

Signed and Sealed this
Fifteenth Day of July, 2025

Coke Morgan Stewart
*Acting Director of the United States Patent and Trademark Office*